United States Patent [19]

Pedrazzi

[11] 4,273,707
[45] Jun. 16, 1981

[54] MONOAZO AND DISAZO DYES CONTAINING AT LEAST ONE SULFO GROUP AND AT LEAST TWO BASIC OR CATIONIC GROUPS

[75] Inventor: Reinhard Pedrazzi, Allschwil, Switzerland

[73] Assignee: Sandoz Ltd., Basel, Switzerland

[21] Appl. No.: 31,781

[22] Filed: Apr. 20, 1979

[30] Foreign Application Priority Data

Apr. 26, 1978 [CH] Switzerland ............... 4500/78
Apr. 26, 1978 [CH] Switzerland ............... 4501/78

[51] Int. Cl.$^3$ .................. C09B 31/02; C09B 29/22
[52] U.S. Cl. .................. 260/187; 260/152; 260/153; 260/156; 260/191
[58] Field of Search ............. 260/187, 191, 152, 153, 260/156

[56] References Cited

U.S. PATENT DOCUMENTS

| | | | |
|---|---|---|---|
| 3,663,538 | 5/1972 | Lebkucher | 260/240 B |
| 3,996,282 | 12/1976 | Jefferies et al. | 260/567.6 M |
| 4,006,131 | 2/1977 | Uehlinger | 260/187 |
| 4,083,840 | 4/1978 | Schoefberger | 260/187 |
| 4,143,034 | 3/1979 | Jefferies | 260/160 |
| 4,153,598 | 5/1979 | Crounse | 260/185 |

*Primary Examiner*—John F. Niebling
*Attorney, Agent, or Firm*—Gerald D. Sharkin; Richard E. Vila; Melvyn M. Kassenoff

[57] ABSTRACT

Compounds of the formula $$(HO_3S)_m-\left[F\begin{matrix}(Z_1-X)_n\\ \\ [Z_2(X)_2]_p\end{matrix}\right]$$

wherein
F is the residue of a monoazo or disazo compound,
each X is independently $-NR_2-Q-NR_3R_4$ or $-NR_2-Q-N^{\oplus}R_5R_6R_7$,
wherein Q is linear or branched $C_{2-6}$alkylene,
$R_2$ is hydrogen or $C_{1-4}$alkyl,
each of $R_3$, $R_4$, $R_5$ and $R_6$ is independently hydrogen; $C_{1-6}$alkyl; $C_{2-6}$alkyl substituted by hydroxy or cyano; $C_{1-3}$alkyl substituted by phenyl or substituted phenyl having 1 to 3 substituents selected from chloro, $C_{1-4}$alkyl and $C_{1-4}$alkoxy; $C_{5-6}$cycloalkyl or $C_{5-6}$cycloalkyl substituted by 1 to 3 $C_{1-4}$alkyl groups, with the proviso that neither $R_5$ nor $R_6$ can be hydrogen, or
$R_3$ and $R_4$ or $R_5$ and $R_6$ taken together and with the nitrogen atom to which they are joined form a 5- or 6-membered ring containing at most one further hetero atom, and
$R_7$ is $C_{1-4}$alkyl or benzyl,
each $Z_1$ is independently $-CO-$, $-SO_2-$ or

[structure: triazine ring with Y substituent and $-N(R_1)-$ linkage]

wherein
$R_1$ is hydrogen or $C_{1-4}$alkyl, and
Y is chloro, hydroxy, amino or an aliphatic or aromatic amino group,
each $Z_2$ is independently

[structure: triazine ring with $-N(R_1)-$ linkage]

wherein $R_1$ is hydrogen or $C_{1-4}$alkyl,
m is 1 or 2,
n is 0–4, and
p is 0–3,
with the proviso that $n+2p \geq m+1$,
are useful as dyes for paper, leather and cellulosic fibers.

34 Claims, No Drawings

MONOAZO AND DISAZO DYES CONTAINING AT LEAST ONE SULFO GROUP AND AT LEAST TWO BASIC OR CATIONIC GROUPS

This invention relates to azo dyes containing sulphonic acid groups and also basic and/or cationic groups.

The invention provides compounds of formula I

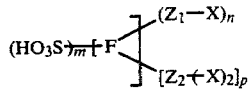

in which
F is the residue of a mono- or dis-azo compound;
each $Z_1$, independently, is a divalent group of the formula —CO—, —SO$_2$—

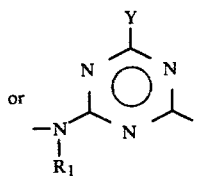

in which
Y is Cl, OH, NH$_2$ or an aliphatic or aromatic amino group,
and R$_1$ is hydrogen or C$_{1-4}$alkyl;
each $Z_2$, independently, is a trivalent group of the formula

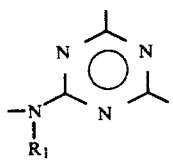

in which R$_1$ is as defined above;
each X, independently, is a basic group —NR$_2$—Q—NR$_3$R$_4$ or a cationic group —NR$_2$—Q—N$^\oplus$R$_5$R$_6$R$_7$,
in which
R$_2$ is hydrogen or C$_{1-4}$alkyl,
Q is linear or branched C$_{2-6}$alkylene,
R$_3$ and R$_4$ are independently hydrogen, unsubstituted C$_{1-6}$alkyl, C$_{2-6}$alkyl substituted by hydroxy or CN, C$_{1-3}$alkyl substituted by phenyl which is unsubstituted or substituted by up to 3 substituents selected from chlorine, C$_{1-4}$alkyl and C$_{1-4}$alkoxy, or C$_{5-6}$cycloalkyl unsubstituted or substituted by up to 3 C$_{1-4}$alkyl groups
or R$_3$ and R$_4$, together with the N atom to which they are attached, form a 5- or 6-membered saturated heterocyclic ring, which may contain one further hetero atom,
R$_5$ and R$_6$ may independently have any of the above significances of R$_3$ and R$_4$ other than hydrogen,
R$_7$ is C$_{1-4}$alkyl or benzyl;
m is 1 or 2,
n is 0 or an integer from 1 to 4, and
p is 0 or an integer from 1 to 3,
whereby (n+2p)≧m+1.

In compounds of formula I, the m sulphonic acid groups may react with groups X to form internal salts of the type (XH)$^\oplus$SO$_3^\ominus$ or X$^\oplus$SO$_3^\ominus$. The compounds of formula I have more basic and/or cationic groups than sulphonic acid groups, and the additional basic and/or cationic groups may form external salts, thus rendering the compounds water-soluble.

In the residue of a mono- or dis-azo compound represented by F, the diazo component radical may belong to the aromatic carbocyclic or aromatic heterocyclic series, as for example the aniline, aminonaphthalene, aminodibenzofuran or benzothiazolylaminophenyl series, the aniline series being preferred. The terminal coupling component radical preferably belongs to the naphthalene series and is preferably derived from 1-naphthol-3- or -4-sulphonic acid or a derivatives thereof, particularly 6-amino-1-naphthol-3-sulphonic acid or a derivatives formed by reaction at the amino group thereof.

In residues of disazo compounds, the central component radical preferably belongs to the phenylene, naphthylene or tetrahydronaphthylene series, more preferably the 1,4-phenylene series.

F may also for example be the residue of a disazo compound in which the coupling component radical or diazo component radical of two monoazo compounds are connected together directly or through a bridging group.

The sulphonic acid groups may be located in the diazo and/or in the coupling component radical and optionally also in the central component radical or bridging group. Preferably, however, the coupling component radical carries at least one sulphonic acid group, more preferably one only.

The (n+2p) X groups, which may be the same or different, are connected through the polyvalent groups Z$_1$ and Z$_2$ to the diazo component radical and/or the terminal coupling component radical of the group F. Where Z$_1$ is Z$_1'$, i.e. —CO— or —SO$_2$—, then the group —Z$_1'$—X (for convenience referred to as X$_I$) is preferably located on the diazo component radical. For a diazo component radical of the aniline series, two groups X$_I$ are preferably attached as in formula IIa or IIb

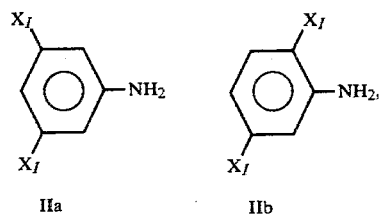

IIa     IIb in which the groups X$_I$ are preferably identical, and preferably there is no, or only one, further substituent on the benzene ring.

The groups —Z$_1''$—X or

together represented for convenience as X$_{II}$, in which Z$_1''$ is the divalent group

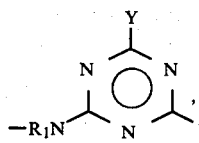

are preferably located in the diazo component radical and/or the terminal coupling component radical, it being particularly preferred that the latter contains at least one such group. For a diazo component of the aniline series, formulae IIIa and IIIb are preferred.

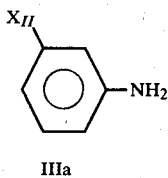
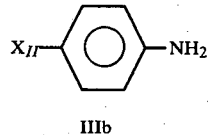

In formula IIIa, one further substituent may be located preferably at the 2-, 4- or 6-position or two further substituents may be located preferably at the 2,5-positions. In formula IIIb there is preferably one additional substituent, which may be in any position.

When the terminal coupling component radical carries a group $X_{II}$, this is preferably derived from a compound of formula IV

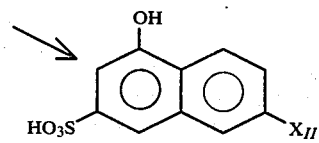

in which the arrow shows the position at which coupling occurs.

The alkylene group Q is preferably linear and more preferably is an ethylene or propylene group.

Where groups $R_1$ and $R_2$ are alkyl, they are preferably methyl. $R_1$ and $R_2$ are preferably $R_1'$ and $R_2'$, where $R_1'$ and $R_2'$ are independently methyl or hydrogen, more preferably hydrogen.

The groups $R_3$ and $R_4$ are preferably identical. When they are $C_{1-6}$alkyl groups, they may be straight-chain or branched and are preferably $C_{1-4}$alkyl, more preferably methyl or ethyl. Cyano- and hydroxy-substituted $C_{2-6}$alkyl groups are preferably substituted ethyl and propyl in which the substituent is other than at the α-position. When $R_3$ and $R_4$ are phenylalkyl, they are preferably benzyl, the phenyl group being preferably unsubstituted. When $R_3$ and $R_4$ are cycloalkyl, they are preferably cyclohexyl; where the cyclohexyl is alkyl substituted, the substituents are preferably methyl. Where $R_3$ and $R_4$, together with the nitrogen atom to which they are attached, form a heterocyclic ring, this is preferably a pyrrolidine, piperidine or morpholine ring.

Preferably $R_3$ and $R_4$ are $R_3'$ and $R_4'$ where $R_3'$ and $R_4'$ are independently hydrogen, linear or branched $C_{1-6}$alkyl, linear hydroxy $C_{2-3}$alkyl or benzyl, or together with the N atom form a pyrrolidine, piperidine or morpholine ring. More preferred significances are $R_3''$ and $R_4''$, which are independently hydrogen, linear or branched $C_{1-4}$alkyl or hydroxyethyl, or together with the N atom form a piperidine or morpholine ring. Particularly preferred significances of $R_3$ and $R_4$ are $R_3'''$ and $R_4'''$, where $R_3'''$ and $R_4'''$ are independently methyl or ethyl.

Groups $R_5$ and $R_6$ are also preferably identical, and the preferred significances given above for $R_3$ and $R_4$ apply equally to $R_5$ and $R_6$, except that $R_5$ and $R_6$ may not be hydrogen.

Where $R_7$ is alkyl it is preferably methyl or ethyl, more preferably methyl. $R_7$ is preferably $R_7'$ where $R_7'$ is methyl, ethyl or benzyl, particularly methyl.

Where X is a basic group $-NR_2-Q-NR_3R_4$,
it is preferably $X_a = -NR_2'-Q-NR_3'R_4'$;
more preferably $X_b = -NR_2'-Q-NR_3''R_4''$;
still more preferably $X_c = -NR_2'-(CH_2)_{2-6}-NR_3''R_4''$;
particularly $X_d = -NR_2'-(CH_2)_{2 \text{ or } 3}-NR_3'''R_4'''$,
in which $R_2'$ is preferably hydrogen.

Where X is a cationic group $-NR_2-Q-N^{\oplus}R_5R_6R_7$, then the preferred significances are as $X_a$-$X_d$ above in which $R_5$ and $R_6$ are as $R_3$ and $R_4$, and $R_7$ is $R_7'$. Particularly preferred is the group $X_e = -NR_2'-(CH_2)_{2 \text{ or } 3}-N^{\oplus}(CH_3)_3$.

Where X is a cationic group the corresponding anion is either a $-SO_3^{\ominus}$ group in the molecule or an external anion $A^{\ominus}$. The nature of $A^{\ominus}$ is not critical; it should however be non-chromophoric. Examples of suitable anions $A^{\ominus}$ are chloride, bromide, iodide, methanesulphonate, ethanesulphonate sulphonate and hydrogen sulphate.

Where Y is an aliphatic amino group, it is preferably a monoalkylamino or dialkylamino group in which the alkyl groups have from 1-4 carbon atoms, may be linear or branched, and may be unsubstituted or substituted by Cl, Br, phenyl or, preferably, hydroxy; or Y may be a $C_{5-6}$cycloalkylamino group. Where Y is an aromatic amino group, it is preferably an anilino group, which may be unsubstituted or substituted in the phenyl ring by one or two substituents selected from halogen (preferably chlorine), $C_{1-4}$alkyl, $C_{1-4}$alkoxy, hydroxy and phenoxy.

Y is preferably $Y_a$ where $Y_a$ is Cl, OH, $NH_2$, mono($C_{1-4}$)alkylamino, monohydroxy($C_{2-4}$)alkylamino, di($C_{1-2}$(alkylamino; bis[hydroxy($C_{2-4}$)alkyl]amino or anilino. More preferably Y is $Y_b$ where $Y_b$ is Cl, OH or anilino.

As stated above, $X_I$ signifies $-CO-X$ or $-SO_2X$, and $X_{II}$ signifies

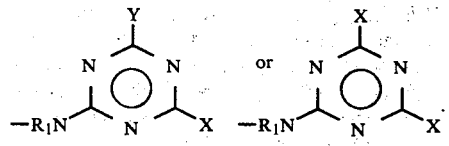

Preferred significances of the groups $X_I$ are, independently, $X_{Ia}$ = $-CO-X_a$ or $-SO_2-X_a$;
more preferably $X_{Ib}$ = $-CO-X_b$ or $-SO_2-X_b$;
still more preferably $X_{Ic}$ = $-CO-X_c$;
and particularly $X_{Id}$ = $-CO-X_d$, in which $R_2'$ is preferably hydrogen.

This order of preferences applies also for cationic groups, in which however $X_I$ is most preferably $X_{Ie}$ where $X_{Ie}$ is $-CO-X_e$.

Preferred significances of the groups $X_{II}$ are, independently, $X_{IIa}=$

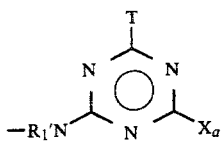

where T is $X_a$ or $Y_a$, in which $Y_a$ is more preferably $Y_b$;

more preferably $X_{IIb}=$

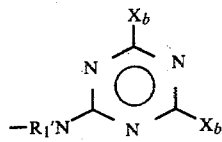

still more preferably $X_{IIc}=$

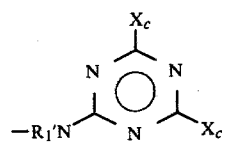

and particularly $X_{IId}=$

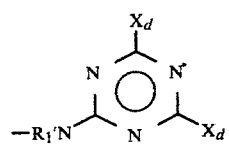

in which $R_1'$ and $R_2'$ are preferably hydrogen.

This order of preferences applies also for cationic groups, in which however $X_{II}$ is most preferably $X_{IIe}$, where $X_{IIe}$ is

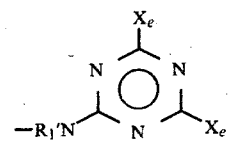

A group of preferred compounds of formula I are those of formula Ia

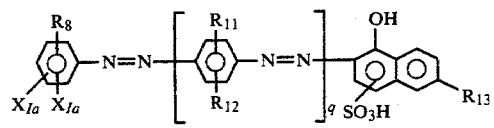

in which the groups $X_{Ia}$ are preferably identical, $R_8$ is hydrogen, $C_{1-4}$alkyl, $C_{1-4}$alkoxy, halogen, mono($C_{1-4}$alkyl)amino, di($C_{1-4}$alkyl)amino, $-SO_2NR_1R_1$ or $-CONR_1R_1$, where $R_1$ is as defined above;

$R_{11}$ is hydrogen, halogen (preferably chlorine), $C_{1-4}$alkyl, $C_{1-4}$alkoxy, $-NHCO-(C_{1-4}$alkyl), $-NHCONH_2$, $-NHCO(CH_2)_{1-3}N(C_{1-4}$alkyl$)_2$ or $-NHCO(CH_2)_{1-3}N^\oplus(CH_3)_3$ $A^\ominus$ where $A^\ominus$ is an anion;

$R_{12}$ is hydrogen, $C_{1-4}$alkyl or $C_{1-4}$alkoxy;

$R_{13}$ is hydrogen, $NH_2$, ($C_{1-4}$alkyl)carbonylamino, benzoylamino whose phenyl ring may be substituted with up to 2 substituents selected from halogen, $NO_2$, $NH_2$, $C_{1-4}$alkyl and $C_{1-4}$alkoxy, or

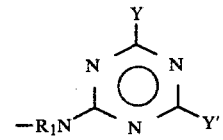

where $R_1$ and Y are as defined above and Y' has any significance of Y other than Cl;

and q is 0 or 1.

$R_8$ is preferably $R_8'$ where $R_8'$ is hydrogen, methyl, methoxy or chlorine, more preferably hydrogen.

In the group

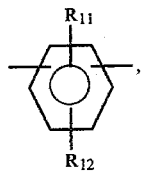

the phenylene linkages may be in the 1,3- or 1,4-positions; preferably the group has the structure

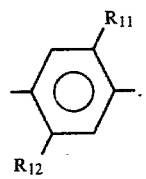

$R_{11}$ is preferably $R_{11}'$ where $R_{11}'$ is hydrogen, methyl or methoxy.

$R_{12}$ is preferably $R_{12}'$ where $R_{12}'$ is hydrogen, methyl or methoxy.

$R_{13}$ is preferably $R_{13}'$ where $R_{13}'$ is hydrogen, $NH_2$, acetylamino or unsubstituted benzoylamino.

Preferred compounds of formula Ia are those in which (1) $X_{Ia}$ is $X_{Ib}$, more preferably $X_{Ic}$ and particularly $X_{Id}$ or $X_{Ie}$ (2) $R_8$ is $R_8'$, particularly hydrogen (3) the group

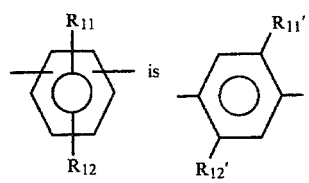

(4) $R_{13}$ is $R_{13}'$, and (5) the $X_I$ groups are in the 2,5- or 3,5-positions, counting from the carbon atom bearing the azo group.

Another group of preferred compounds of formula I are those of formula Ib

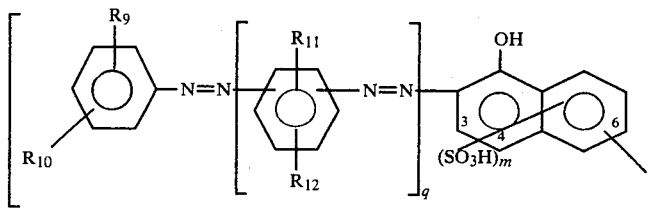
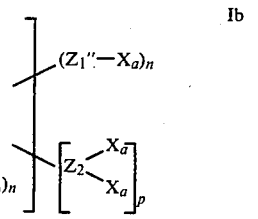

in which the basic or cationic groups may be the same or different and are preferably located at the positions indicated in formulae IIIa, IIIb and/or IV above, $R_9$ is hydrogen, halogen, $C_{1-4}$alkyl, $C_{1-4}$alkoxy, phenoxy, —NHCOR$_{14}$, —SO$_2$R$_{14}$, —SO$_2$NR$_1$R$_1$ or —CONR$_1$R$_1$, where R$_1$ is as defined above, in which R$_{14}$ is $C_{1-4}$alkyl or phenyl;

$R_{10}$ is hydrogen, halogen, $C_{1-4}$alkyl or $C_{1-4}$alkoxy;

r is 0 or 1;

and $R_{11}$, $R_{12}$, $R_{13}$, $Z_1''$, $Z_2$, $X_a$, m, n, p and q are as defined above.

Preferably $R_9$ is $R_9'$ where $R_9'$ is hydrogen, chlorine, methyl, methoxy, acetylamino, benzoylamino, —SO$_2$NH$_2$ or —CONH$_2$. More preferably it is $R_9''$, where $R_9''$ is hydrogen, chlorine, methyl, methoxy, acetylamino or benzoylamino, particularly hydrogen.

$R_{10}$ is preferably $R_{10}'$ where $R_{10}'$ is hydrogen, chlorine, methyl or methoxy, particularly hydrogen.

Preferably $R_{11}$, $R_{12}$ and $R_{13}$ are, independently, $R_{11}'$, $R_{12}'$ and $R_{13}'$. The group $R_{13}$ is preferably in position 6. If r=0, then preferably a —$Z_1''$—$X_a$ or —$Z_2$—$(X_a)_2$ group occupies position 6. Preferably m=1, and in this case the sulpho group is in position 3 or 4, preferably in position 3.

Preferred compounds of formula Ib are those in which, independently, (1) $R_9$ is $R_9'$, more preferably $R_9''$, particularly hydrogen,
(2) $R_{10}$ is $R_{10}'$, particularly hydrogen,
(3) the group

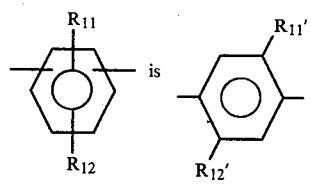

(4) $R_{13}$ is $R_{13}'$ in position 6, or
(5) r=0, and a basic or cationic group is in position 6,
(6) the groups $X_a$ are preferably $X_b$, more preferably $X_c$, particularly $X_d$ or $X_e$,
(7) m=1 and the sulpho group is in position 3.

More preferred compounds of formula Ib are those of formula Ic

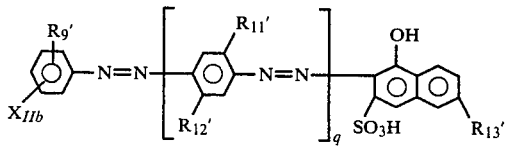

in which $X_{IIb}$ and $R_9'$ are as defined above.

Particularly preferred compounds of formula Ic are those in which, independently, (1) $R_9'$ is $R_9''$, particularly hydrogen,
(2) $X_{IIb}$ is $X_{IIc}$, more preferably $X_{IId}$ or $X_{IIe}$,
(3) $R_{11}'$ and $R_{12}'$ are hydrogen.

A further group of more preferred compounds of formula Ib are those of formula Id

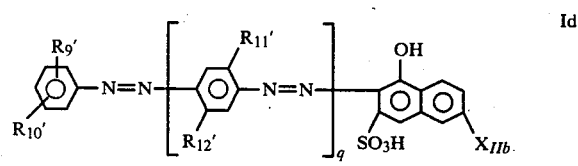

particularly those in which, independently,
(1) $R_9'$ is $R_9''$ and $R_{10}'$ is hydrogen,
(2) $X_{IIb}$ is $X_{IIc}$, more preferably $X_{IId}$ or $X_{IIe}$,
(3) $R_{11}'$ and $R_{12}'$ are hydrogen,
(4) q=1.

Other groups of preferred compounds of formula I are those of formula Ie

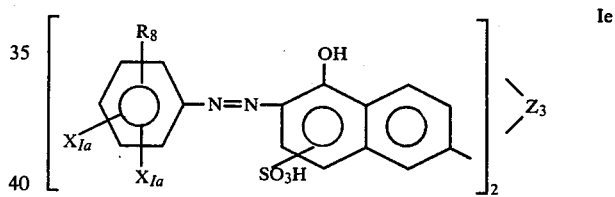

wherein the groups $X_{Ia}$ are preferably identical, and $Z_3$ is a divalent N-containing bridging group.

The variables in the two parts of the molecule connected by $Z_3$ may be the same or different but are preferably the same.

$Z_3$ is preferably $Z_{3a}$ where $Z_{3a}$ is —NH—; —NHCONH—;

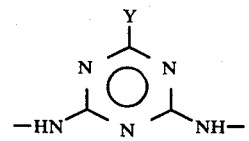

in which Y is as defined above and is preferably $Y_c$ where $Y_c$ is Cl, NH$_2$ or —NH—phenyl;

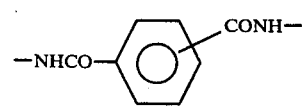

containing a 1,3- or 1,4-phenylene group; —NHCOCH$_2$CH$_2$CONH—; or —NHCOCH=CHCONH—. More preferably it is $Z_{3b}$ where $Z_{3b}$ is —NHCONH—;

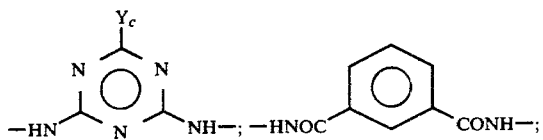

—NHCOCH$_2$CH$_2$CONH— or —NHCOCH=CH-CONH—; particularly preferred is Z$_{3c}$, i.e. —NH-CONH—,

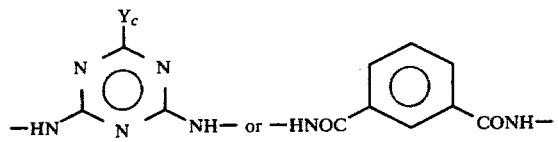

Preferred compounds of formula Ie are those in which, independently,
(1) R$_8$ is R$_8'$, particularly hydrogen,
(2) X$_{Ia}$ is X$_{Ib}$, more preferably X$_{Ic}$ and particularly X$_{Id}$ or X$_{Ie}$,
(3) Z$_3$ is Z$_{3a}$, preferably Z$_{3b}$, particularly Z$_{3c}$,
(4) Groups X$_{Ia}$ are in the 2,5- or 3,5-positions with respect to the carbon atom bearing the azo group.

A further group of preferred compounds of formula I are those of formula If

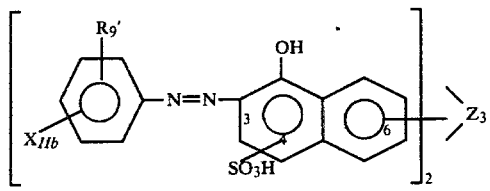

in which R$_9'$, X$_{IIb}$ and Z$_3$ are as defined above, and X$_{IIb}$ preferably occupies the positions shown in formulae IIIa and b. The variables in the two parts of the molecule joined by bridging group Z$_3$ may be the same or different, but are preferably the same.

Preferred compounds of formula If are those in which, independently,
(1) R$_9'$ is R$_9''$, particularly hydrogen,
(2) X$_{IIb}$ is X$_{IIc}$, particularly X$_{IId}$ or X$_{IIe}$,
(3) Z$_3$ is Z$_{3a}$, more preferably Z$_{3b}$, particularly Z$_{3c}$,
(4) the sulpho group is in position 3, the bridging group Z$_3$ is in position 6 and both parts of the molecule joined by Z$_3$ are identical.

A still further preferred group of compounds of formula I have formula Ig

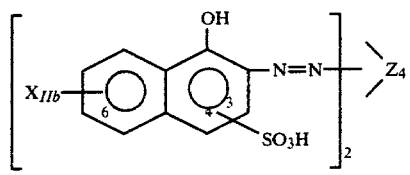

in which the bridging group Z$_4$ is 1,3- or 1,4-phenylene or a group of the formula

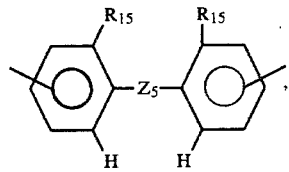

where
R$_{15}$ is hydrogen, chlorine, methyl or methoxy, particularly hydrogen,
and Z$_5$ is a direct bond, —(CH$_2$)$_t$, —O—, —O(CH$_2$-)$_t$O—, —SO$_2$—, —NHCO—, —NHCONH—, —NHCO(CH$_2$)$_t$CONH— or —CONH(CH$_2$)$_t$NHCO—, where t is 2 or 3, preferably 2.

Z$_4$ is preferably Z$_{4a}$ where Z$_{4a}$ is 3,3'- or 4,4'-phenylene,

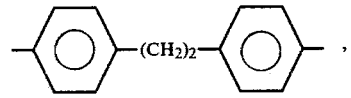

1,3- or 1,4-

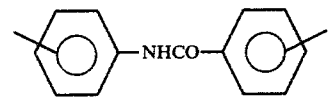

or 1,3- or 1,4-

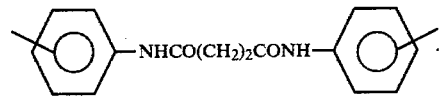

Preferred compounds of formula Ig are those in which
(1) X$_{IIb}$ is X$_{IIc}$, particularly X$_{IId}$ or X$_{IIe}$,
(2) Z$_4$ is Z$_{4a}$, and
(3) the sulpho group is in position 3, and group X$_{IIb}$ in position 6, and the two parts of the molecule are identical.

The invention also provides a process for the preparation of compounds of formula I comprising the step of coupling to a corresponding terminal coupling component a corresponding diazotised amine or monoazoamine, the necessary n (—Z$_1$—X) and/or p

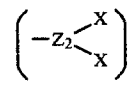

groups being already present in the coupling component and/or the diazo component.

Compounds of formula I containing X$_{II}$ groups, for example compounds of formula Ib, Ic, Id, If or Ig, may also be prepared by reacting a compound of formula V

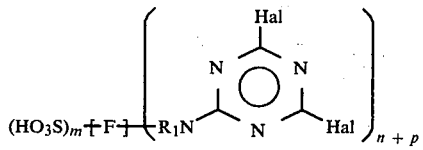

in which Hal is halogen, particularly chlorine, in any desired order with n+2p moles of a diamine of formula VIa and/or formula VIb

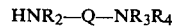

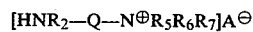

and optionally with n moles of a compound HY'.

In all the above definitions, the term "halogen" signifies fluorine, chlorine or bromine.

The processes, of which the former is preferred, are carried out in conventional manner. Thus the coupling reaction may be carried out in weakly acid or weakly alkaline aqueous media, and the products may be isolated and purified in known manner.

The compounds of formula I may be transformed into water-soluble salt forms by treating the basic compounds with at least a stoichiometric quantity of an organic or inorganic acid. In the compounds of formula I, free basic (i.e. non-protonated) X groups may also be treated with alkylating agents containing the group $R_7$ to give quaternary ammonium-containing cationic X groups.

The starting diazo and coupling components are either known or can be obtained from available starting materials by known or analogous processes. Thus, for example, the diazo components containing groups $X_I$ for the compounds of formula Ia or Ie may be prepared by reaction of the corresponding nitrophenylcarboxylic acid chloride or nitrophenyl sulphonylchloride with stoichiometric amounts of one or more diamines of formula VIa and/or VIb and finally reducing the nitro group to an amino group.

The diazo components containing group $X_{II}$ for the compounds of formulae Ib, Ic and If may for example be prepared by reaction of cyanuric halide with an optionally substituted nitroaniline, a diamine of formula VIa and/or VIb and optionally a compound HY' in any desired order, and finally reducing the nitro group.

Similarly, the group $X_{II}$-containing coupling components for compounds of formula Ib, Id or Ig may be obtained by condensing a cyanuric halide with the corresponding amino-containing coupling component, diamine of formula VIa and/or VIb and optionally compound HY' in any desired order.

Compounds of formula I in the form of their water-soluble acid salts are dyestuffs useful for dyeing or printing substrates consisting of or containing cellulosic fibres, for example cotton, or preferably for the dyeing or printing of paper. They may also be used for dyeing or printing leather, particularly vegetable-tanned low-affinity leather.

Cotton may for example be dyed by an exhaust dyeing process at room temperature to the boil or printed with printing pastes of conventional type. Sized or unsized paper may be printed or dyed in the mass during the manufacturing process or by the dipping process. Leather may be dyed in conventional manner.

Compounds of formula I may also be used in the form of liquid or solid dye compositions. They may be produced in the form of stable liquid, preferably aqueous, compositions by known methods, preferably by solution in a suitable solvent, optionally in the presence of an auxiliary, for example a stabilizer. Such compositions may for example be prepared as disclosed in French Patent 1,572,030. A suitable liquid composition is for example the following (parts are by weight):

- 100 parts compound of formula I as acid salt
- 1–100, preferably 1–10, parts inorganic salt
- 1–100 parts of an organic acid, e.g. formic, acetic, lactic or citric acid
- 100–800 parts water
- 0–500 parts of a solubilising agent, for example glycols such as diethylene, triethylene or hexylene glycol; glycol ethers such as Methyl Cellosolve, Methyl Carbitol, polyglycol; urea; formamide; dimethylformamide, etc.

The compounds of formula I may also be prepared in solid, preferably granular, form, preferably by granulating as described in French Patent No. 1,581,900. A suitable solid composition is for example the following (parts are by weight):

- 100 parts compound of formula I as acid salt
- 1–100, preferably 1–10, parts inorganic salt
- 0–800 parts of a filler, preferably a nonionic material such as dextrin, sugar, glucose or urea.

The solid compositions may contain up to 10% residual moisture.

The dyestuffs of formula I, in the form of their acid salts, have good solubility properties, particularly good solubility in cold water. When used in paper-making, they colour the waste water only slightly or not at all, which is desirable for ecological reasons. They do not give mottling of the dyed paper and are insensitive to pH over wide ranges. The resulting dyeings on paper are brilliant and are characterised by good light-fastness; after long illumination the shades change tone-in-tone. The dyed paper is fast not only to water but also to milk, fruit juices and sweetened mineral water; because of the good alcohol fastness of the dyes (particularly those of formulae Ie, If and Ig), it is also resistant to alcoholic drinks.

The dyes exhibit high substantivity, that is they exhaust practically quantitatively on the substrate. They may be added to the paper mass directly in the form of a dry powder or granulate, without first making up a solution, without loss of brilliance or yield. The dyes according to the invention may also be used in soft water without loss of yield.

Fibrous materials containing wood pulp are dyed with the dyestuffs according to the invention in as good and level quality as with purely cationic dyes.

The dyed paper is both oxidatively and reductively bleachable, which is important for the recycling of waste paper.

The following Examples, in which solid materials are given as parts by weight and liquids as parts by volume, all percentages are weight percentages and temperatures are in degrees Centigrade, illustrate the invention.

PREPARATION OF STARTING MATERIALS

EXAMPLE (A)

106 Parts 5-nitroisophthalic acid are stirred into 300 parts chlorobenzene containing 0.5 parts triethylamine and warmed to 80° C.; finally 80 parts thionyl chloride are slowly added dropwise. After stirring 3 hours at 80°, the temperature is raised slowly to 120°. When all is dissolved, the solution is cooled to 90° and a mixture of 137 parts 3-dimethylaminopropylamine and 60 parts chlorobenzene is added dropwise; finally 53 parts sodium carbonate are added. The resulting suspension is stirred 2 hours at 100°, cooled and treated with 100 parts water. The mixture is acidified to pH 5 with 30% hydrochloric acid and the chlorobenzene removed by steam distillation.

The residual aqueous solution is made alkaline, causing the nitro product to separate as an oil, which is taken up in ethyl acetate, washed with brine, dried and evaporated to give a brown oil. The oil is dissolved in 200 parts water and 120 parts 30% hydrochloric acid, and this solution is added dropwise to a hot suspension of 100 parts iron turnings, 100 parts water and 10 parts 30% HCl. After 2 hours at 95°–98° the reduction is complete. Sodium carbonate is added to make the mixture alkaline to brilliant yellow indicator, and the product is filtered hot. The filtrate (~520 parts by volume) contains 110 parts of the compound of the formula

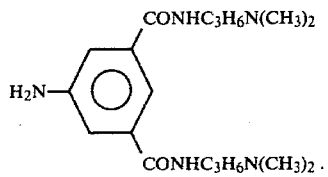

EXAMPLE (B)

If example (a) is repeated using nitroterephthalic acid, the product is the compound of the formula

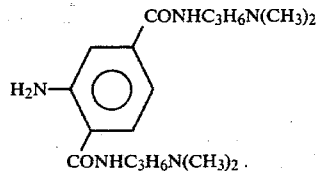

EXAMPLE (C)

92 Parts cyanuric chloride are dissolved in 750 parts acetone and cooled to 0°–5°. 69 Parts 3-nitroaniline are added, then 130 parts of a 4 N sodium carbonate solution are added dropwise over an hour. The mixture is stirred for an hour, then 600 parts of ice water are added. The resulting suspension is filtered and the moist residue is added slowly in small portions to 250 parts 3-dimethylaminopropylamine. The temperature of the mixture rises to 60°–70°, giving a syrupy solution which is stirred for 1 hour at 90°–100° and then diluted to 1000 parts by volume by addition of ice. The aqueous phase is separated off, and the resinous residue is stirred with 200 parts water and 90 parts 30% HCl, giving an aqueous suspension with a pH of 5.

In a second vessel 300 parts of water, 70 parts iron turnings and 20 parts 30% HCl are stirred together for 1 hour. The weakly acid suspension prepared as above is added, and the temperature is held for 2 hours at 95°–98°. The product is made alkaline to brilliant yellow by adding sodium carbonate and filtered hot. The yellow-brown filtrate (~950 parts by volume) contains 155 parts of the compound of the formula

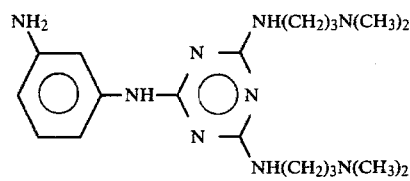

In place of the 3-nitroaniline, the following nitro compounds may also be used to produce corresponding products: 4-nitroaniline, 2-chloro- or 2-bromo-4-nitroaniline, 2-methyl-4-nitroaniline, 2-methoxy-4-nitroaniline, 2-methyl-3-nitroaniline, 4-chloro-3-nitroaniline, 4-methyl-3-nitroaniline, 4-methoxy-3-nitroaniline, 2-methyl-5-nitroaniline, 2-methoxy-5-nitroaniline or 5-chloro-2-methoxy-3-nitroaniline.

EXAMPLE (D)

A mixture of water and ice (125 parts each) is stirred with 92 parts cyanuric chloride to give a fine dispersion. 130 Parts 3-diethylaminopropylamine is added dropwise over 3 hours, at a rate such that the temperature does not exceed 5°. The product is stirred for 1 hour at 45°–50° and treated with 100 parts 30% caustic soda solution, causing the product to separate as a white mass which is suction filtered and washed with water. After drying in vacuum at 60°, 150 parts of 2,4-diamino-N,N'-bis-(3-diethylaminopropyl)-6-chloro-1,3,5-triazine are obtained.

This product is dissolved in 600 parts water and 106 parts 30% HCl, and 95 parts 6-amino-1-naphthol-3-sulphonic acid is added followed by 100 parts sodium acetate. The mixture is heated to 90°–95°, the pH sinking from 4.5 to 3.7. After 3 hours the reaction is complete, and on cooling a clear brown solution containing 210 parts of the compound of the formula is obtained.

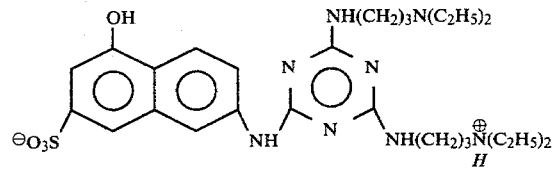

The use of alternative diamines in the process of examples a–d gives rise to the corresponding alternative diazo components or coupling components as shown in Table 1.

TABLE 1

| Diamine | reacted with 5-nitroisophthalic acid and reduced gives diazo component: | reacted with nitroterephthalic acid and reduced gives diazo component: | reacted with the condensation product of cyanuric chloride and 3-nitroaniline and reduced gives the diazo component: | reacted with cyanuric chloride and 6-amino-1-naphthol-3-sulphonic acid gives the coupling component: |
|---|---|---|---|---|
| $H_2N-(CH_2)_3-N(CH_3)_2$ | $D_{1a}$ (Example (a)) | $D_{1b}$ (Example (b)) | $D_{1c}$ (Example (c)) | $K_{2d}$ |

TABLE 1-continued

| Diamine | reacted with 5-nitro-isophthalic acid and reduced gives diazo component: | reacted with nitro-terephthalic acid and reduced gives diazo component: | reacted with the condensation product of cyanuric chloride and 3-nitroaniline and reduced gives the diazo component: | reacted with cyanuric chloride and 6-amino-1-naphthol-3-sulphonic acid gives the coupling component: |
|---|---|---|---|---|
| $H_2N-(CH_2)_3-N(C_2H_5)_2$ | $D_{2a}$ | $D_{2b}$ | $D_{2c}$ | $K_{1d}$ (Example (d)) |
| $H_2N-(CH_2)_2-N(CH_3)_2$ | $D_{3a}$ | $D_{3b}$ | $D_{3c}$ | $K_{3d}$ |
| $H_2N-(CH_2)_2-N(C_2H_5)_2$ | $D_{4a}$ | $D_{4b}$ | $D_{4c}$ | $K_{4d}$ |
| $H_2N-(CH_2)_2-\overset{\oplus}{N}(CH_3)_3 Cl^{\ominus}$ | $D_{5a}$ | $D_{5b}$ | $D_{5c}$ | $K_{5d}$ |
| $H_2N-(CH_2)_2-N\begin{smallmatrix}CH_3\\C_2H_5\end{smallmatrix}$ | $D_{6a}$ | $D_{6b}$ | $D_{6c}$ | $K_{6d}$ |
| $H_2N-(CH_2)_2-N\begin{smallmatrix}CH(CH_3)_2\\CH(CH_3)_2\end{smallmatrix}$ | $D_{7a}$ | $D_{7b}$ | $D_{7c}$ | $K_{7d}$ |
| $H_2N-(CH_2)_2-N\begin{smallmatrix}CH_2CH_2CH(CH_3)_2\\CH_2CH_2CH(CH_3)_2\end{smallmatrix}$ | $D_{8a}$ | $D_{8b}$ | $D_{8c}$ | $K_{8d}$ |
| $H_2N-(CH_2)_2-N\begin{smallmatrix}(CH_2)_5CH_3\\(CH_2)_5CH_3\end{smallmatrix}$ | $D_{9a}$ | $D_{9b}$ | $D_{9c}$ | $K_{9d}$ |
| $H_2N-(CH_2)_2-N\bigcirc H$ | $D_{10a}$ | $D_{10b}$ | $D_{10c}$ | $K_{10d}$ |
| $\overset{CH_3}{\underset{HN-(CH_2)_4-N(C_2H_5)_2}{\mid}}$ | $D_{11a}$ | $D_{11b}$ | $D_{11c}$ | $K_{11d}$ |
| $H_2N-(CH_2)_5-N(C_2H_5)_2$ | $D_{12a}$ | $D_{12b}$ | $D_{12c}$ | $K_{12d}$ |
| $H_2N-(CH_2)_6-N(CH_3)_2$ | $D_{13a}$ | $D_{13b}$ | $D_{13c}$ | $K_{13d}$ |
| $H_2N-(CH_2)_3-N(CH_2CH_2OH)_2$ | $D_{14a}$ | $D_{14b}$ | $D_{14c}$ | $K_{14d}$ |

Diazo components as listed in column 4 but prepared using 4-nitroaniline are designated $D_{1c'}-D_{14c'}$ and those prepared using 4-methyl-3-nitroaniline are designated $D_{1c''}-D_{14c''}$.

EXAMPLE 1

24 Parts by volume of the solution prepared as in Example c) are treated with 20 parts ice and 3 parts 30% HCl and diazotised with 10 parts 1 N sodium nitrite solution at 0°–5°. The diazonium salt solution is added dropwise to a mixture of 3 parts 6-acetylamino-1-naphthol-3-sulphonic acid ($K_1$) and 100 parts water, maintaining the pH at 7–8 by addition of sodium carbonate solution. An orange dyestuff suspension is obtained. When no more diazonium salt can be detected, the suspension is treated with zinc chloride until the run-off of a spot test has become almost colourless. The dyestuff is filtered off and dried at 80° in a vacuum. the product of the formula

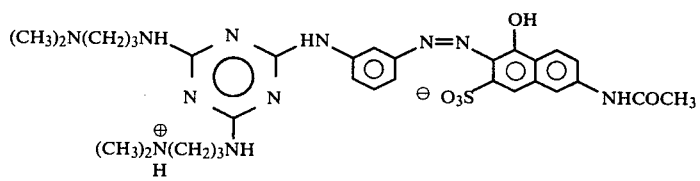

is obtained in the form of a powder which is easily soluble in weakly acid to acid aqueous media and dyes paper in red-orange tones. The dyed paper has good light- and wet-fastness.

EXAMPLE 2

If instead of 24 parts of the solution of Example (c), 18 parts of the solution obtained in Example (a) is used in Example 1, a dyestuff having the formula

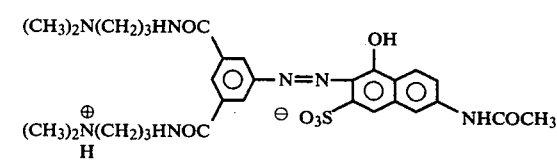

is obtained in the form of a powder which is soluble in acidic aqueous media and gives on paper yellow-orange dyeings having good light and wet fastness.

EXAMPLES 3–27

Following the procedure of Example 1 and using the coupling and diazo components listed in Table 2 below, further monoazo dyestuffs can be obtained which dye paper in the colours indicated, with good light- and wet-fastness.

| Abbreviations used for colors: | |
|---|---|
| yo = yellow-orange | bo = brown-orange |
| r = red | bor = bordeaux red |
| brv = brilliant red-violet | o = orange |
| or = orange-red | blr = bluish-red |
| br = brown-red | v = violet |
| ro = red-orange | sr = scarlet red |
| bbr = brilliant bluish-red | rv = red-violet |

TABLE 2

| Example No. | Coupling Component | Diazo Component | Colour |
|---|---|---|---|
| 3 | 6-benzoylamino-1-naphthol-3-sulfonic acid (K$_2$) | D$_{1c}$ | ro |
| 4 | 1-naphthol-3-sulfonic acid (K$_3$) | " | ro |
| 5 | 1-naphthol-4-sulfonic acid (K$_4$) | " | ro |
| 6 | K$_1$ | D$_{1c'}$ | blr |
| 7 | K$_2$ | D$_{1c'}$ | blr |
| 8 | K$_3$ | " | blr |
| 9 | K$_4$ | " | blr |
| 10 | K$_1$ | D$_{1c''}$ | r |
| 11 | K$_2$ | " | r |
| 12 | K$_3$ | " | r |
| 13 | K$_4$ | " | r |
| 14 | K$_1$ | D$_{2c}$ | ro |
| 15 | K$_2$ | " | ro |
| 16 | K$_3$ | " | ro |
| 17 | K$_4$ | " | ro |
| 18 | K$_1$ | D$_{2c'}$ | blr |
| 19 | K$_2$ | " | blr |
| 20 | K$_3$ | " | blr |
| 21 | K$_4$ | " | blr |
| 22 | K$_1$ | D$_{1b}$ | ro |
| 23a | K$_2$ | D$_{1a}$ | yo |
| 23b | K$_2$ | D$_{1b}$ | ro |
| 24a | K$_3$ | D$_{1a}$ | yo |
| 24b | K$_3$ | D$_{1b}$ | ro |
| 25a | K$_4$ | D$_{1a}$ | yo |
| 25b | K$_4$ | D$_{1b}$ | ro |
| 26 | K$_1$ | D$_{2a}$ | yo |
| 27 | K$_3$ | D$_{2b}$ | yo |

Similarly, coupling components K$_1$—K$_4$ can be reacted with any of the diazo components listed in Table 1 to give dyestuffs which give dyeings on paper with good light- and wet-fastness.

EXAMPLE 28

67 Parts by volume of the solution prepared in Example (a) are treated with 50 parts ice and 10 parts 30% HCl and diazotised at 0°–5° with 10.5 parts 4 N sodium nitrite solution. To the diazonium salt solution is added 50 parts ice and enough sodium acetate to hold the pH at 3.5. Then 4.7 parts 3-methylaniline are added and the mixture stirred at pH 3–3.5 until no more diazonium salt is detectable. The dyestuff solution is made alkaline with caustic soda, and the dyestuff which comes out of solution is separated and dissolved in 300 parts water and 20 parts 30% HCl.

The intermediate product is diazotised with 9 parts of 4 N sodium nitrite solution at room temperature, and the diazo solution is added dropwise to a suspension of 13.6 parts 6-benzoylamino-1-naphthol-3-sulphonic acid in 500 parts of water, keeping the pH at 7–7.5. As soon as no more diazonium salt is detectable, the blue-red dyestuff solution is treated with zinc chloride to give a filterable suspension. By filtration and vacuum drying at 60° is obtained in powder form the dyestuff of the formula

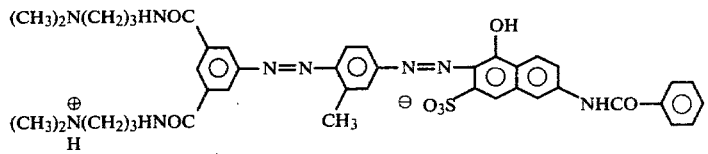

which is soluble in acidic aqueous media and dyes paper in bordeaux red shades; the dyeings have good light- and wet-fastness.

EXAMPLE 29

When 90 parts of the solution of Example (c) are used in place of the 67 parts of the solution of Example (a) the dyestuff of the formula

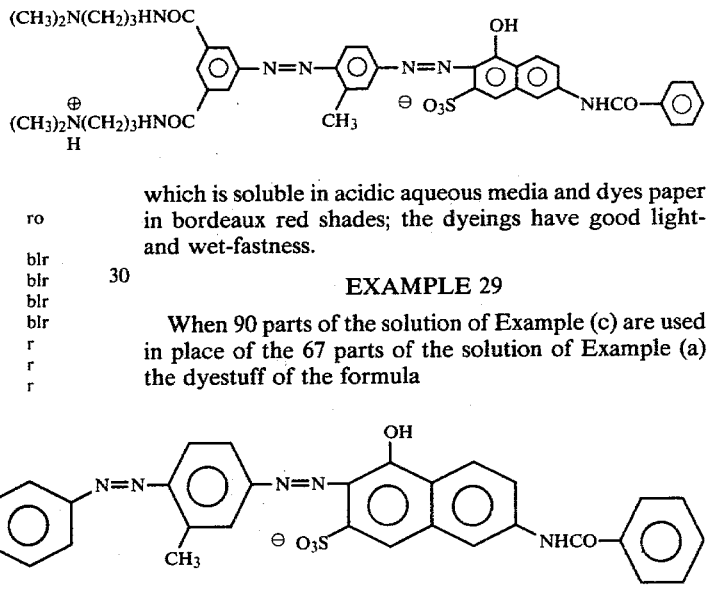

is obtained, which dyes paper in blue-red shades, with good light- and wet-fastness properties.

EXAMPLES 30–47

Following the procedure of Example 28 and using the diazo, middle and terminal coupling components given in Table 3 below, disazo dyestuffs are obtained which dye paper in fast shades of the colours indicated.

TABLE 3

| Example No. | Diazo Component | Middle Component | Terminal Coupling Component (see Table 2) | Colour |
|---|---|---|---|---|
| 30 | D$_{1c}$ | aniline | K$_4$ | br |
| 31 | " | 2-methoxyaniline | " | rv |
| 32 | " | " | K$_3$ | brv |
| 33 | D$_{2c'}$ | 3-methylaniline | " | v |
| 34 | " | aniline | K$_1$ | v |
| 35 | D$_{2c}$ | 2-methoxyaniline | " | br |
| 36 | D$_{1a}$ | 3-methylaniline | K$_3$ | bbr |
| 37 | D$_{2a}$ | " | " | bbr |
| 38a | D$_{1a}$ | " | K$_1$ | r |
| 38b | " | " | K$_4$ | br |
| 39 | D$_{2a}$ | " | K$_1$ | r |
| 40 | D$_{1b}$ | " | K$_1$ | r |

TABLE 3-continued

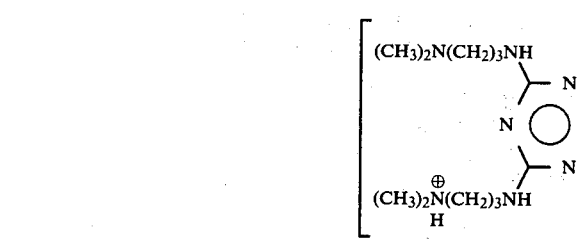

| Example No. | Diazo Component | Middle Component | Terminal Coupling component (see Table 2) | Colour |
|---|---|---|---|---|
| 41 | $D_{2a}$ | aniline | " | bo |
| 42 | $D_{2b}$ | " | " | r |
| 43 | $D_{1a}$ | " | " | bo |
| 44 | $D_{1b}$ | aniline | $K_1$ | bo |
| 45 | $D_{3a}$ | " | " | bo |
| 46 | $D_{1a}$ | 2-methoxyaniline | " | rv |
| 47 | $D_{2a}$ | " | " | rv |

Similarly, any other combinations of the diazo components listed in Table 1 with coupling components $K_1$–$K_4$ and the middle components listed in Table 3 give disazo dyestuffs which dye paper in brown-red to red-violet or bordeaux red to brilliant blue-red shades, the dyeings having good fastness properties.

EXAMPLE 48

3.15 Parts of the compound of the formula

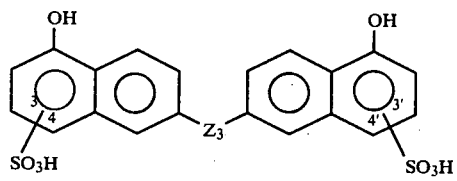

in which $Z_3$ is —NHCONH— and the sulphonic acid groups are in the 3,3'-positions are dispersed in 200 parts water. The solution obtained in Example (c) (35.5 parts) is diazotised and added dropwise over 30 minutes, keeping the pH at 7–8 by addition of sodium carbonate. After 1 hour the product is filtered and dried in a vacuum at 60°, giving the dyestuff of the formula

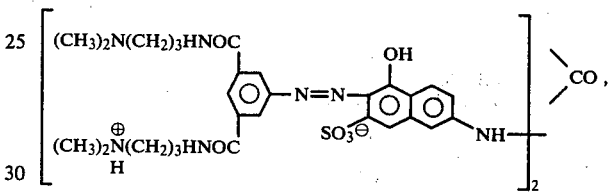

which is soluble in acidic aqueous media and gives orange dyeings on paper having particularly good wet-fastness and very good fastness to alcohol.

EXAMPLE 49

If, instead of 35.5 parts of the product of Example (c), 21.1 parts of the product of Example (a) is taken, a dyestuff is obtained having the formula

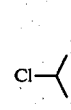

which is soluble in acidic aqueous media and gives orange dyeings on paper having good wet fastness, in particular good fastness to alcohol.

EXAMPLES 50–78

In manner analogous to Example 48, corresponding compounds may be prepared using a diazo component given in column 2 of Table 4 below and a coupling component of the formula given in Example 48, in which the bridging group $Z_3$ and the position of the sulphonic acid groups are given in columns 3 and 4 of the Table. The colour of the dyeings obtained on paper is indicated in column 5; such dyeings show good wet- and alcohol-fastness.

TABLE 4

| Example No. | Diazo Component | $Z_3$ | Position of Sulfo Groups | Colour |
|---|---|---|---|---|
| 50 | $D_{1c}$ | —HNCOCH=CHCONH— | 3,3' | ro |
| 51 | " | 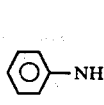 | " | o |
| 52 | " | (triazine with NH—phenyl and NH—) | " | o |
| 53 | " | —HNCO—(phenyl)—CONH— | " | bo |
| 54 | " | —HNCOC$_2$H$_4$CONH— | " | o |
| 55 | " | —NH— | " | blr |
| 56 | $D_{2c}$ | —NHCONH— | " | o |

TABLE 4-continued

| Example No. | Diazo Component | $Z_3$ | Position of Sulfo Groups | Colour |
|---|---|---|---|---|
| 57 | " | " | 4,4' | o |
| 58 | " | —HNCO—C$_6$H$_4$—CONH— | " | bo |
| 59 | $D_{1c}$ | " | 3,3' | bor |
| 60 | " | triazine with NH-phenyl and two NH— substituents | " | bor |
| 61 | " | —HNCOCH=CHCONH— | " | rv |
| 62 | $D_{2c}$ | —HNCONH— | " | bor |
| 63 | " | —HNCO—C$_6$H$_4$—CONH— (meta) | " | br |
| 64 | " | —HNCOC$_2$H$_4$CONH— | " | blr |
| 65 | $D_{4c}$ | —HNCOC$_2$H$_4$CONH— | " | o |
| 66 | " | —HNCONH— | " | o |
| 67 | $D_{1b}$ | " | " | o |
| 68 | $D_{2a}$ | " | " | o |
| 69 | $D_{2a}$ | " | 4,4' | o |
| 70 | $D_{3a}$ | " | 3,3' | o |
| 71a | $D_{1a}$ } | —HNCOCH=CHCONH— | " | { o |
| 71b | $D_{2a}$ | | | o |
| 72a | $D_{1a}$ } | triazine with Cl and two NH— | " | { o |
| 72b | $D_{2a}$ | | | o |
| 73a | $D_{1a}$ } | triazine with NH-phenyl and two NH— | " | { ro |
| 73b | $D_{2a}$ | | | ro |
| 74a | $D_{1a}$ } | —HNCO—C$_6$H$_4$—CONH— (meta) | " | { ro |
| 74b | $D_{2a}$ | | | ro |
| 75a | $D_{1a}$ } | " | 4,4' | { ro |
| 75b | $D_{2a}$ | | | ro |
| 76a | $D_{1a}$ } | —NH— | 3,3' | { bbr |
| 76b | $D_{1b}$ | | | bbr |
| 77a | $D_{1a}$ } | —HNCOC$_2$H$_4$CONH— | " | { o |
| 77b | $D_{1b}$ | | | o |
| 78a | $D_{2a}$ } | " | " | { o |
| 78b | $D_{2b}$ | | | o |

Analogous dyes with similar properties may be made using any of the above-indicated coupling components with any of the diazo components listed in Table 1.

EXAMPLE 79

6.2 Parts of 4-methoxyaniline are dissolved in 100 parts water and 25 parts 30% HCl and cooled to 0°–5°. To the solution is added dropwise 50 parts of in sodium nitrite solution.

In a second reaction vessel is placed 140 parts by volume of the solution prepared as in Example (d), and the above diazo solution is added dropwise at pH 6–6.5. The mixtue is stirred overnight, then treated with 90 parts sodium chloride and 15 parts zinc chloride. The dyestuff is filtered and vacuum dried at 60° to give a powder of the formula

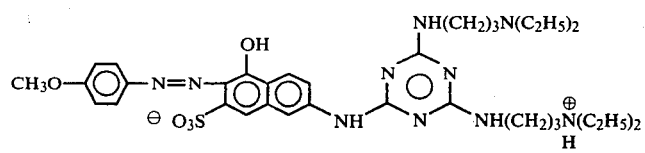

which is soluble in acidic aqueous media and dyes paper in scarlet red shades, the dyeings having good light- and wet-fastness.

EXAMPLES 80–97

In manner analogous to Example 79, analogous monoazo compounds may be prepared using the diazo components and coupling components given in Table 5 below. The resulting compounds dye paper in the indicated shades, the dyeings having good light- and wet-fastness.

TABLE 5

| Example No. | Diazo Component | Coupling Component | Colour |
|---|---|---|---|
| 80 | 4-methoxyaniline | $K_{2d}$ | sr |
| 81a | 2-methoxyaniline | $K_{1d}$ | ro |
| 81b | " | $K_{2d}$ | ro |
| 82a | 1-amino-4-benzoylamino-benzene | $K_{1d}$ | blr |
| 82b | 1-amino-4-benzoylamino-benzene | $K_{2d}$ | blr |
| 83a | 1-amino-4-acetylamino-benzene | $K_{1d}$ | blr |
| 83b | 1-amino-4-acetylamino-benzene | $K_{2d}$ | blr |
| 84a | 4-aminodiphenylether | $K_{1d}$ | ro |
| 84b | " | $K_{2d}$ | ro |
| 85a | 2,5-dimethoxyaniline | $K_{1d}$ | blr |
| 85b | " | $K_{2d}$ | blr |
| 86 | " | $K_{3d}$ | blr |
| 87a | 2,5-dimethylaniline | $K_{1d}$ | o |
| 87b | " | $K_{2d}$ | o |
| 88a | 2-methoxy-5-methylaniline | $K_{1d}$ | r |
| 88b | " | $K_{2d}$ | r |
| 89 | " | $K_{4d}$ | r |
| 90a | aniline | $K_{1d}$ | yo |
| 90b | " | $K_{2d}$ | yo |
| 91 | " | $K_{4d}$ | yo |
| 92a | 3-chloro-4-methylaniline | $K_{1d}$ | o |
| 92b | " | $K_{2d}$ | o |
| 93 | 2-aminonaphthalene sulfonamide | $K_{1d}$ | ro |
| 94 | 4-methylaniline | $K_{1d}$ | o |
| 95a | 4-aminobenzanilide | $K_{1d}$ | yo |
| 95b | " | $K_{2d}$ | yo |
| 96 | 2-(4'-aminophenyl)-6-methylbenzothiazole | $K_{2d}$ | ro |
| 97 | 2-aminodibenzofuran | $K_{2d}$ | o |

Analogous compounds may be prepared by the use of the above diazo components with the other coupling components listed in Table 1.

EXAMPLE 98

9.9 Parts 4-aminoazobenzene are stirred overnight, with 100 parts water and 25 parts 30% HCl and diazotised by adding dropwise 50 parts of the IN sodium nitrite solution. In a second reaction vessel is placed 140 parts by volume of a solution containing 28 parts of the compound described in Example (d), together with 30 parts sodium acetate. The diazo solution is added dropwise at pH 3–4, and the mixture is stirred overnight then treated with 50 parts 30% caustic soda to bring the pH to 8–9. After stirring for 1 hour, the precipitated dyestuff is filtered and dried to give a powder of the formula

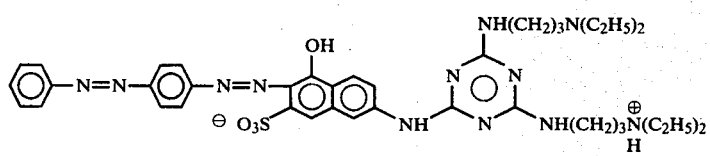

which is soluble in acidic aqueous media and gives bluish-red dyeings on paper which exhibit good light- and wet-fastness.

EXAMPLES 99–111

In manner analogous to Example 98 and using the diazo components, middle components and terminal coupling components given in Table 6 below, corresponding dyestuffs are obtained which dye paper in the indicated shades, the dyeings having good light- and wet-fastness.

TABLE 6

| Ex. No. | Diazo Component | Middle Component | Terminal Coupling Component | Colour |
|---|---|---|---|---|
| 99 | aniline | aniline | $K_{2d}$ | blr |
| 100a | " | " | $K_{3d}$ | blr |
| 100b | " | " | $K_{4d}$ | blr |
| 101a | "2-methoxyaniline | " | $K_{1d}$ | rv |
| 101b | " | " | $K_{2d}$ | rv |
| 102a | " | 3-methylaniline | $K_{1d}$ | bor |
| 102b | " | " | $K_{2d}$ | bor |
| 103a | 2,5-dimethoxy-aniline | aniline | $K_{1d}$ | blr |
| 103b | 2,5-dimethoxy-aniline | " | $K_{2d}$ | blr |
| 104a | 4-methylaniline | " | $K_{1d}$ | blr |
| 104b | " | " | $K_{2d}$ | blr |
| 105a | " | " | $K_{3d}$ | blr |
| 105b | " | " | $k_{4d}$ | blr |
| 106a | 4-methylaniline | 2-methoxyaniline | $K_{1d}$ | rv |
| 106b | " | " | $K_{2d}$ | rv |
| 107a | 1-amino-4-acetyl-aminobenzene | aniline | $K_{1d}$ | blr |
| 107b | 1-amino-4-acetyl-aminobenzene | " | $K_{2d}$ | blr |
| 108a | 3-chloro-4-methyl-aniline | 3-methylaniline | $K_{1d}$ | br |
| 108b | 3-chloro-4-methyl-aniline | " | $K_{2d}$ | br |
| 109a | 3-aminobenzene-sulfonamide | 2-methoxyaniline | $K_{1d}$ | v |
| 109b | 3-aminobenzene-sulfonamide | " | $K_{2d}$ | v |
| 110a | 3-aminobenzamide | aniline | $K_{1d}$ | blr |
| 110b | " | " | $K_{2d}$ | blr |
| 111a | 3-aminophenyl-methylsulfone | " | $K_{1d}$ | blr |
| 111b | 3-aminophenyl- | " | $K_{2d}$ | blr |

TABLE 6-continued

| Ex. | Middle | Terminal Coupling |
|---|---|---|
| No. | Diazo Component | Component | Component | Colour |
| | methylsulfone | | | |

Analogous compounds may be prepared using the diazo and middle components listed in Table 6 with the remaining coupling components listed in Table 1.

EXAMPLE 112

A diazo solution is prepared by adding 27 parts of a 4 N sodium nitrite solution dropwise to a suspension of 15 parts 3-aminoacetanilide in 100 parts water and 25 parts 30% HCl at 0°–5°. This diazo solution is poured into a mixture of 60 parts of the solution prepared in Example (d), 200 parts water and 100 parts ice, holding the pH at 3–3.5 by dropwise addition of 70 parts 4N sodium carbonate solution. After 2 hours 45 parts 65% sulphuric acid is added and the mixture is stirred for 3 hours at 85°, by which time the cleavage of the acetyl group is practically complete. The solution is cooled to room temperature and treated with 15 parts zinc chloride and, after 10 minutes, 60 parts common salt.

The resulting dyestuff is filtered off, stirred in 300 parts water and 20 parts 30% HCl and diazotised with 25 parts of 4 N sodium nitrite solution. The diazo solution is then added to 60 parts of the solution prepared as in Example (d), 300 parts water and 100 parts ice, at a pH of 4–4.5. When coupling is complete, the solution is made alkaline with caustic soda, and the precipitated dyestuff filtered and dried. The resulting compound has the formula

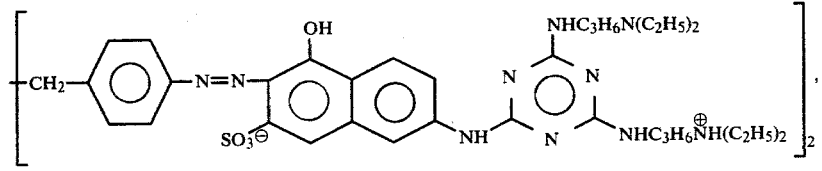

has good solubility in acidic aqueous media and dyes paper in orange shades having excellent wet- and alcohol-fastness.

EXAMPLE 113

10.6 Parts 4,4'-diaminodibenzyl are dissolved in 300 parts water and 25 parts 30% HCl, cooled to 0°–5° and tetraazotised with 27 parts 4 N sodium nitrite. The mixture is treated with aminosulphonic acid to destroy residual nitrous acid, and the tetraazo solution is poured into a mixture of 60 parts of the product of Example (d), 700 parts water and 75 parts salt, keeping the pH at 4–5 by addition of ~50 parts sodium acetate. After coupling the dyestuff was precipitated with caustic soda, filtered and dried. The resulting dyestuff, of the formula $$\left[-CH_2-\underset{}{\bigcirc}-N=N-\underset{SO_3^{\ominus}}{\overset{OH}{\bigcirc\bigcirc}}-NH-\underset{N}{\overset{NHC_3H_6N(C_2H_5)_2}{\underset{N}{\bigcirc}}}-NHC_3H_6\overset{\oplus}{N}H(C_2H_5)_2\right]_2$$

has good soubility in acidic aqueous media, and gives on paper red-orange dyeings having extremely good wet- and alcohol-fastness.

EXAMPLES 114–128

In manner analogous to Example 113, corresponding dyestuffs are produced from the diamines and coupling components listed in Table 7 below. The resulting dyestuffs give dyeings on paper of the shades indicated, having good wet fastness and particularly good fastness to alcohol.

TABLE 7

| Example No. | Tetraazo Component | Coupling Component | Colour |
|---|---|---|---|
| 114a | H$_2$N—⌬—NHCOC$_2$H$_4$CONH—⌬—NH$_2$ | K$_{1d}$ | ro |
| 114b | " | K$_{2d}$ | ro |
| 115a | H$_2$N—⌬—NHCOC$_3$H$_6$CONH—⌬—NH$_2$ | " | ro |
| 115b | " | " | ro |
| 116a | H$_2$N⌬—NHCOC$_2$H$_4$CONH—⌬NH$_2$ | " | yo |
| 116b | " | " | yo |
| 117 | H$_2$N—⌬—C$_2$H$_4$—⌬—NH$_2$ | " | ro |
| 118 | " | K$_{4d}$ | ro |
| 119a | H$_2$N—⌬—C$_3$H$_6$—⌬—NH$_2$ | K$_{1d}$ | ro |

TABLE 7-continued

| Example No. | Tetraazo Component | Coupling Component | Colour |
|---|---|---|---|
| 119b | " | $K_{2d}$ | ro |
| 120a | $H_2N-\bigcirc-CONHC_2H_4NHCO-\bigcirc-NH_2$ | $K_{1d}$ | yo |
| 120b | " | $K_{2d}$ | yo |
| 121a | $H_2N-\bigcirc-NHCO-\bigcirc-NH_2$ | $K_{1d}$ | blr |
| 121b | " | $K_{2d}$ | blr |
| 122as | $H_2N-\bigcirc-NHCO-\bigcirc(NH_2)$ | $K_{1d}$ | yo |
| 122b | " | $K_{2d}$ | yo |
| 123a | " | $K_{1d}$ | o |
| 123b | " | $K_{2d}$ | o |
| 124a | $H_2N-\bigcirc-NHCONH-\bigcirc(NH_2)$ | $K_{1d}$ | o |
| 124b | " | $K_{2d}$ | o |
| 125a | $H_2N-\bigcirc-OC_2H_4O-\bigcirc-NH_2$ | $K_{1d}$ | r |
| 125b | " | $K_{2d}$ | r |
| 126a | $H_2N-\bigcirc-O-\bigcirc-NH_2$ | $K_{1d}$ | or |
| 126b | " | $K_{2d}$ | or |
| 127a | $H_2N-\bigcirc-SO_2-\bigcirc-NH_2$ | $K_{1d}$ | o |
| 127b | " | $K_{2d}$ | o |
| 128a | $H_2N-\bigcirc-\bigcirc-NH_2$, $OCH_3$ $OCH_3$ | $K_{1d}$ | v |
| 128b | " | $K_{2d}$ | v |

Analogous dyestuffs may be prepared using the other coupling components listed in Table 1.

EXAMPLE 129

45 Parts of the dyestuff of Example 98 are dissolved in 500 parts water containing 3.4 parts glacial acetic acid. The resulting solution is evaporated to dryness, giving the dyestuff salt of the formula

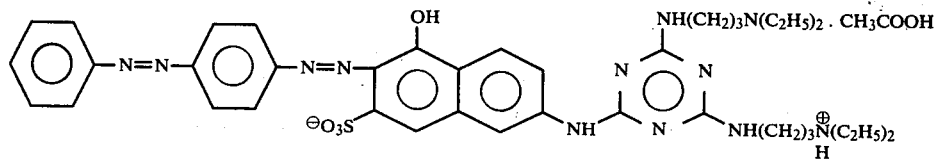

which has high solubility in cold water. Similarly, hydrochloric, sulphuric, phosphoric, formic and lactic acids may be used instead of acetic acid to give corresponding salts. The dyestuffs of the other examples may similarly be converted to salt forms.

EXAMPLE 130

80 Parts of the dyestuff salt of Example 129 are added to a solution of 20 parts dextrin and 20 parts glacial acetic acid in 500 parts water, and stirred to give a homogeneous suspension. Spray drying produces a blue-red granulate which is very soluble in water and which dyes paper in bluish-red shades.

The salt forms of the dyestuffs of the other examples may be converted to granulates in similar manner.

EXAMPLE 131

120 Parts of the dyestuff salt of Example 129 are added to a mixture of 150 parts butylpolyglycol, 50 parts glacial acetic acid and 600 parts water and dissolved by warming to 60°. The solution is filtered, cooled to room temperature and made up to 1000 parts with water. The resulting dye concentrate solution is storable for several months at room temperature and may be used directly or after dilution with water for dyeing paper in bluish-red shades.

Salts of the dyestuffs of the other examples may be similarly worked up into stable liquid dye preparations.

APPLICATION EXAMPLE A

70 Parts of chemically bleached sulphite cellulose obtained from pinewood and 30 parts of chemically bleached sulphite cellulose obtained from birchwood are ground in 2000 parts of water in a Hollander. 0.5 Pats of the dyestuff from Example 36 (as an acid addition salt, e.g. according to Example 129) are sprinkled into this pulp. Paper is produced from this pulp after mixing for 20 minutes. The absorbent paper which is obtained in this manner is dyed in a bluish-red shade. The waste water is practically colourless.

APPLICATION EXAMPLE B 0.5 Parts of the dyestuff from Example 98 (as an acid addition salt, e.g. according to Example 129) are dissolved in 100 parts of hot water and cooled to room temperature. This solution is added to 100 parts of chemically bleached sulphite cellulose which have been ground in a Hollander with 2000 parts of water. Sizing takes place after thorough mixing for 15 minutes. The paper which is produced from this material has a bluish-red shade and good light- and wet-fastness.

APPLICATION EXAMPLE C

An absorbent length of unsized paper is drawn at 40°-50° through a dyestuff solution having the following composition:

0.5 parts of the dyestuff from Example 36 (as an acid addition salt, e.g. according to Example 129)
0.5 parts of starch and
99.0 parts of water.

The excess dyestuff solution is squeezed out through two rollers. The dried length of paper is dyed in a bluish-red shade.

The dyestuffs of the remaining examples may also be used for dyeing according to Application Examples A–C.

APPLICATION EXAMPLE D

100 Parts freshly tanned and neutralised chrome leather are agitated for 30 minutes in a vessel with a dyebath of 250 parts water at 55° and 0.5 parts of the dyestuff of Example 98 in acid addition salt form, and then treated in the same bath for 30 minutes with 2 parts of an anionic fatty liquor based on sulphonated train oil. The leather is then dried and prepared in the normal way, giving a leather evenly dyed in a bluish-red shade.

Other low affinity vegetable-tanned leathers can similarly be dyed by known methods.

APPLICATION EXAMPLE E

2 Parts of the dyestuff of Example 98 in acid addition salt form are dissolved in 4000 parts demineralised water at 40°. 100 Parts of a cotton textile substrate are added, and the bath is raised to boiling point over 30 minutes and held at the boil for 1 hour. After rinsing and drying, a bluish-red dyeing is obtained having good light- and wet-fastness. The dye exhausts practically quantitatively, and the waste water is almost colourless.

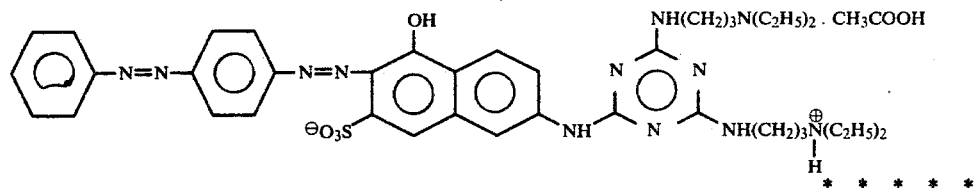

What is claimed is:

1. A compound of the formula (a)

[structure with $R_8$, $R_{11}$, OH, $T_{1a}$, $R_{12}$, $SO_3H$, $R_{13}$]

or (b)

[structure with $R_9$, $R_{10}$, $R_{11}$, $R_{12}$, OH, $(SO_3H)_m$, $R_{13}$, and bracketed $NR_1$–triazine–$T_a$ groups indexed by $n$ and $p$]

or an external salt thereof,
wherein each
$R_1$ is independently hydrogen or $C_{1-4}$alkyl,
$R_8$ is hydrogen, $C_{1-4}$alkyl, $C_{1-4}$alkoxy, halo, $C_{1-4}$alkylamino, di-($C_{1-4}$alkyl)amino, —$SO_2NR_1R_1$ or —$CONR_1R_1$,
  wherein each $R_1$ is independently hydrogen or $C_{1-4}$alkyl,
$R_9$ is hydrogen, halo, $C_{1-4}$alkyl, $C_{1-4}$alkoxy, phenoxy, —$NHCOR_{14}$, —$SO_2R_{14}$, —$SO_2NR_1R_1$ or —$CONR_1R_1$,
  wherein each
  $R_1$ is independently hydrogen or $C_{1-4}$alkyl, and
  $R_{14}$ is $C_{1-4}$alkyl or phenyl,
$R_{10}$ is hydrogen, halo, $C_{1-4}$alkyl or $C_{1-4}$alkoxy,
$R_{11}$ is hydrogen, halo, $C_{1-4}$alkyl, $C_{1-4}$alkoxy, ($C_{1-4}$alkyl)carbonylamino, ureido, —NHCO—($CH_2$)$_k$—N($C_{1-4}$alkyl)$_2$ or —NHCO—($CH_2$)$_k$—N$^\oplus$($CH_3$)$_3$, wherein k is 1, 2 or 3,
$R_{12}$ is hydrogen, $C_{1-4}$alkyl or $C_{1-4}$alkoxy,
$R_{13}$ is hydrogen; amino; ($C_{1-4}$alkyl)carbonylamino; benzamido; substituted benzamido having, on the phenyl ring, 1 or 2 substituents selected from halo, nitro, amino, $C_{1-4}$alkyl and $C_{1-4}$alkoxy; or

[triazine structure: —$NR_1$ attached to ring with $N$, $N$, $N$ and substituents $Y$, $Y'$]

wherein
$R_1$ is hydrogen or $C_{1-4}$alkyl,
Y is chloro, hydroxy, amino or an amino group having at least one aliphatic, cycloaliphatic or aromatic substituent, and
Y' is hydroxy, amino or an amino group having at least one aliphatic, cycloaliphatic or aromatic substituent,
each $T_a$ is independently —$NR_2'$—Q—$NR_3'R_4'$ or —$NR_2'$—Q—$N^\oplus R_5'R_6'R_7'$,
wherein
$R_2'$ is hydrogen or methyl,
each of $R_3'$ and $R_4'$ is independently hydrogen, $C_{1-6}$alkyl, n-$C_{2-3}$-hydroxyalkyl or benzyl,
each of $R_5'$ and $R_6'$ is independently $C_{1-6}$alkyl, n-$C_{2-3}$hydroxyalkyl or benzyl or $R_3'$ and $R_4'$ or $R_5'$ and $R_6'$ taken together and with the nitrogen atom to which they are joined form a pyrrolidine, piperidine or morpholine ring, $R_7'$ is methyl, ethyl or benzyl, and Q is linear or branched $C_{2-6}$alkylene, each $T_{Ia}$ is independently $-CO-T_a$ or $-SO_2-T_a$, wherein $T_a$ is as defined above, each Y is independently chloro, hydroxy, amino or an amino group having at least one aliphatic cycloaliphatic or aromatic substituent, m is 1 or 2, n is 0, 1, 2, 3 or 4, and p is 0, 1, 2 or 3, with the proviso that $n+2p \geq m+1$, with the provisos that (i) the two $-N=N-$ radicals in (a) are meta or para to each other, (ii) the two $-N=N-$ radicals in (b) are meta or para to each other, (iii) each basic group is independently in free base, internal salt or acid addition salt form, (iv) the positive charge of each cationic group is independently balanced by the negative charge of a $-SO_3^{\ominus}$ group of the molecule or an external non-chromophoric anion, and (v) the number of basic groups in internal salt form and cationic groups the positive charge of which is balanced by the negative charge of a $-SO_3^{\ominus}$ group of the molecule does not exceed the number of sulfo groups present in the molecule.

2. A compound according to claim 1 having the formula

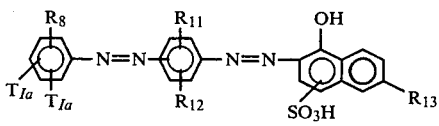

or an external salt thereof, wherein $R_8$ is hydrogen, $C_{1-4}$alkyl, $C_{1-4}$alkoxy, halo, $C_{1-4}$alkylamino, di-$(C_{1-4}$alkyl)amino, $-SO_2NR_1R_1$ or $-CONR_1R_1$, wherein each $R_1$ is independently hydrogen or $C_{1-4}$alkyl, $R_{11}$ is hydrogen, halo, $C_{1-4}$alkyl, $C_{1-4}$alkoxy, ($C_{1-4}$alkyl)carbonylamino, ureido, $-NHCO-(CH_2-)_k-N(C_{1-4}$alkyl$)_2$ or $-NHCO-(CH_2-)_k-N^{\oplus}(CH_3)_3$, wherein k is 1, 2 or 3, $R_{12}$ is hydrogen, $C_{1-4}$alkyl or $C_{1-4}$alkoxy, $R_{13}$ is hydrogen; amino; ($C_{1-4}$alkyl)carbonylamino; benzamido; substituted benzamido having, on the phenyl ring, 1 or 2 substituents selected from halo, nitro, amino, $C_{1-4}$alkyl and $C_{1-4}$alkoxy;

or 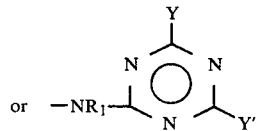

wherein $R_1$ is hydrogen or $C_{1-4}$alkyl,

Y is chloro, hydroxy, amino or an amino group having at least one aliphatic, cycloaliphatic or aromatic substituent, and Y' is hydroxy, amino or an amino group having at least one aliphatic, cycloaliphatic or aromatic substituent, and each $T_{Ia}$ is independently $-CO-T_a$ or $-SO_2-T_a$, wherein $T_a$ is $-NR_2'-Q-NR_3'R_4'$ or $-NR_2'-Q-N^{\oplus}R_5'R_6'R_7'$, wherein $R_2'$ is hydrogen or methyl, each of $R_3'$ and $R_4'$ is independently hydrogen, $C_{1-6}$alkyl, n-$C_{2-3}$hydroxyalkyl or benzyl, each of $R_5'$ and $R_6'$ is independently $C_{1-6}$alkyl, n-$C_{2-3}$hydroxyalkyl or benzyl or $R_3'$ and $R_4'$ or $R_5'$ and $R_6'$ taken together and with the nitrogen atom to which they are joined form a pyrrolidine, piperidine or morpholine ring, $R_7'$ is methyl, ethyl or benzyl, and Q is linear or branched $C_{2-6}$alkylene, with the provisos that (i) the two $-N=N-$ radicals are meta or para to each other, (ii) each basic group is independently in free base, internal salt or acid addition salt form, (iii) the positive charge of each cationic group is independently balanced by the negative charge of the $-SO_3^{\ominus}$ group of the molecule or an external non-chromophoric anion, and (iv) the maximum number of basic groups in internal salt form and cationic groups the positive charge of which is balanced by the negative charge of the $-SO_3^{\ominus}$ group of the molecule is one.

3. A compound according to claim 2, or an external salt thereof, wherein each of $R_3'$ and $R_4'$ is independently hydrogen, $C_{1-6}$alkyl, n-$C_{2-3}$hydroxyalkyl or benzyl, each of $R_5'$ and $R_6'$ is independently $C_{1-6}$alkyl, n-$C_{2-3}$hydroxyalkyl or benzyl or $R_3'$ and $R_4'$ or $R_5'$ and $R_6'$ taken together and with the nitrogen atom to which they are joined are pyrrolidino, piperidino or morpholino, Y is chloro, hydroxy, $-NR_{21}R_{22}$, $C_{5-6}$cycloalkylamino, anilino or substituted anilino having, on the phenyl ring, 1 or 2 substituents selected from halo, $C_{1-4}$alkyl, $C_{1-4}$alkoxy, hydroxy and phenoxy, wherein each of $R_{21}$ and $R_{22}$ is independently hydrogen, $C_{1-4}$alkyl or $C_{1-4}$alkyl substituted by chloro, bromo, phenyl or hydroxy, and Y' is hydroxy, $-NR_{21}R_{22}$, $C_{5-6}$cycloalkylamino, anilino or substituted anilino having, on the phenyl ring, 1 or 2 substituents selected from halo, $C_{1-4}$alkyl, $C_{1-4}$alkoxy, hydroxy and phenoxy, wherein each of $R_{21}$ and $R_{22}$ is independently hydrogen, $C_{1-4}$alkyl or $C_{1-4}$alkyl substituted by chloro, bromo, phenyl or hydroxy.

4. A compound according to claim 3, or an external salt thereof, wherein each $T_{Ia}$ is independently $-CO-X_a$ or $-SO_2-X_a$, wherein $X_a$ is $-NR_2'-Q-NR_3'R_4'$, wherein $R_2'$ is hydrogen or methyl, each of $R_3'$ and $R_4'$ is independently hydrogen, $C_{1-6}$alkyl, n-$C_{2-3}$hydroxyalkyl or benzyl or $R_3'$ and $R_4'$ taken together and with the nitrogen atom to which they are joined are pyrrolidino, piperidino or morpholino, and Q is linear or branched $C_{2-6}$alkylene.

5. A compound according to claim 4, or an external salt thereof, wherein the two $T_{Ia}$'s are identical.

6. A compound according to claim 5 having the formula

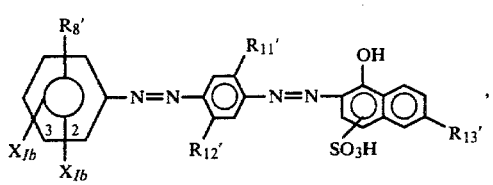

or an external salt thereof,
wherein
R$_8'$ is hydrogen, methyl, methoxy or chloro,
R$_{11}'$ is hydrogen, methyl or methoxy,
R$_{12}'$ is hydrogen, methyl or methoxy,
R$_{13}'$ is hydrogen, amino, acetamido or benzamido, and
each X$_{Ib}$ is —CO—X$_b$ or —SO$_2$—X$_b$,
wherein
X$_b$ is —NR$_2'$—Q—NR$_3''$R$_4''$,
wherein
R$_2'$ is hydrogen or methyl,
each of R$_3''$ and R$_4''$ is independently hydrogen, C$_{1-4}$alkyl or hydroxyethyl or
R$_3''$ and R$_4''$ taken together and with the nitrogen atom to which they are joined are piperidino or morpholino, and
Q is linear or branched C$_{2-6}$alkylene,
with the provisos that the two X$_{Ib}$'s are identical and are in the 2,5- or 3,5-positions,
with the proviso that each basic group is independently in free base, internal salt (maximum of one) or acid addition salt form.

7. A compound according to claim 6, or an external salt thereof,
wherein
each X$_{Ib}$ is —CO—NR$_2'$—(CH$_2$)$_s$—NR$_3''$R$_4''$,
wherein
R$_2'$ is hydrogen or methyl,
each of R$_3''$ and R$_4''$ is independently hydrogen, C$_{1-4}$alkyl or hydroxyethyl or
R$_3''$ and R$_4''$ taken together and with the nitrogen atom to which they are joined are piperidino or morpholino, and
s is 2 to 6, inclusive.

8. A compound according to claim 7, or an external salt thereof, each of R$_3'''$ and R$_4'''$ is independently methyl or ethyl, and
t is 2 or 3.

9. A compound according to claim 8, or an external salt thereof,
wherein
R$_2'$ is hydrogen.

10. The compound according to claim 9 having the formula

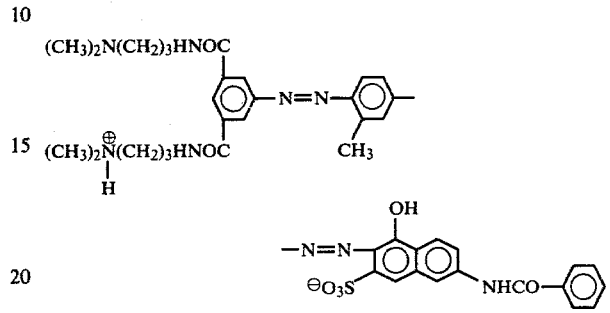

11. An external salt according to claim 3 having the formula

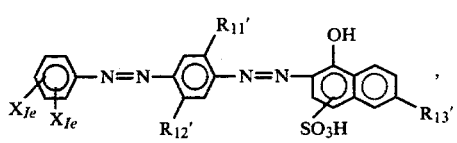

wherein
R$_{11}'$ is hydrogen, methyl or methoxy,
R$_{12}'$ is hydrogen, methyl or methoxy,
R$_{13}'$ is hydrogen, amino, acetamido or benzamido, and
each X$_{Ie}$ is —CO—NR$_2'$—(CH$_2$)$_t$—N$^{\oplus}$(CH$_3$)$_3$,
wherein
R$_2'$ is hydrogen or methyl, and
t is 2 or 3,
with the proviso that the positive charge of each cationic group is independently balanced by the negative charge of the —SO$_3^{\ominus}$ group of the molecule (maximum of one) or an external non-chromophoric anion.

12. An external salt according to claim 11 wherein each R$_2'$ is hydrogen.

13. A compound according to claim 11 having the formula

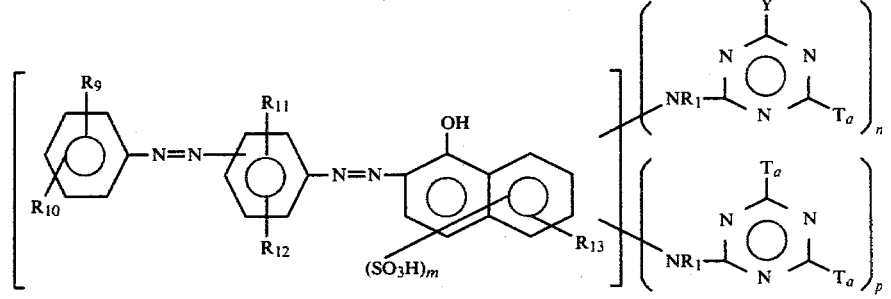

wherein
R$_8'$ is hydrogen, and
each X$_{Ib}$ is —CO—NR$_2'$—(CH$_2$)$_t$—NR$_3'''$R$_4'''$,
wherein
R$_2'$ is hydrogen or methyl, or an external salt thereof,
wherein each
R$_1$ is independently hydrogen or C$_{1-4}$alkyl, $R_9$ is hydrogen, halo, $C_{1-4}$alkyl, $C_{1-4}$alkoxy, phenoxy, —NHCOR$_{14}$, —SO$_2$R$_{14}$, —SO$_2$NR$_1$R$_1$ or —CONR$_1$R$_1$,
wherein each
$R_1$ is independently hydrogen or $C_{1-4}$alkyl, and
$R_{14}$ is $C_{1-4}$alkyl or phenyl,
$R_{10}$ is hydrogen, halo, $C_{1-4}$alkyl or $C_{1-4}$alkoxy,
$R_{11}$ is hydrogen, halo, $C_{1-4}$alkyl, $C_{1-4}$alkoxy, ($C_{1-4}$alkyl)carbonylamino, ureido, —NHCO—(CH$_2$)$_k$—N(C$_{1-4}$alkyl)$_2$ or —NHCO—(CH$_2$)$_k$—N$^\oplus$(CH$_3$)$_3$, wherein k is 1, 2 or 3,
$R_{12}$ is hydrogen, $C_{1-4}$alkyl or $C_{1-4}$alkoxy,
$R_{13}$ is hydrogen; amino; ($C_{1-4}$alkyl)carbonylamino; benzamido; substituted benzamido having, on the phenyl ring, 1 or 2 substituents selected from halo, nitro, amino, $C_{1-4}$alkyl and $C_{1-4}$alkoxy; or

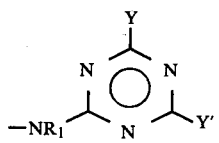

wherein
$R_1$ is hydrogen or $C_{1-4}$alkyl,
Y is chloro, hydroxy, amino or an amino group having at least one aliphatic, cycloaliphatic or aromatic substituent, and
Y' is hydroxy, amino or an amino group having at least one aliphatic, cycloaliphatic or aromatic substituent,
each T$_a$ is independently —NR$_2'$—Q—NR$_3'$R$_4'$ or —NR$_2'$—Q—N$^\oplus$R$_5'$R$_6'$R$_7'$,
wherein
$R_2'$ is hydrogen or methyl,
each of $R_3'$ and $R_4'$ is independently hydrogen, $C_{1-6}$alkyl, n-$C_{2-3}$hydroxyalkyl or benzyl,
each of $R_5'$ and $R_6'$ is independently $C_{1-6}$alkyl, n-$C_{2-3}$hydroxyalkyl or benzyl or
$R_3'$ and $R_4'$ or $R_5'$ and $R_6'$ taken together and with the nitrogen atom to which they are joined form a pyrrolidine, piperidine or morpholine ring,
$R_7'$ is methyl, ethyl or benzyl, and
Q is linear or branched $C_{2-6}$alkylene,
each Y is independently chloro, hydroxy, amino or an amino group having at least one aliphatic, cycloaliphatic or aromatic substituent,
m is 1 or 2,
n is 0, 1, 2, 3 or 4, and
p is 0, 1, 2 or 3,
with the proviso that n+2p≧m+1,
with the proviso that (i) the two —N=N— radicals are meta or para to each other, (ii) each basic group is independently in free base, internal salt or acid addition salt form, (iii) the positive charge of each cationic group is independently balanced by the negative charge of a —SO$_3^\ominus$ group of the molecule or an external non-chromophoric anion, and (iv) the number of basic groups in internal salt form and cationic groups the positive charge of which is balanced by the negative charge of a —SO$_3^\ominus$ group of the molecule does not exceed the number of sulfo groups present in the molecule.

14. A compound according to claim 13, or an external salt thereof,
wherein
each of $R_3'$ and $R_4'$ is independently hydrogen, $C_{1-6}$alkyl, n-$C_{2-3}$hydroxyalkyl or benzyl,
each of $R_5'$ and $R_6'$ is independently $C_{1-6}$alkyl, n-$C_{2-3}$hydroxyalkyl or benzyl or
$R_3'$ and $R_4'$ or $R_5'$ and $R_6'$ taken together and with the nitrogen atom to which they are joined are pyrrolidino, piperidino or morpholino,
each Y is independently chloro, hydroxy, —NR$_{21}$R$_{22}$, C$_{5-6}$cycloalkylamino, anilino or substituted anilino having, on the phenyl ring, 1 or 2 substituents selected from halo, $C_{1-4}$alkyl, $C_{1-4}$alkoxy, hydroxy and phenoxy,
wherein
each of $R_{21}$ and $R_{22}$ is independently hydrogen, $C_{1-4}$alkyl or $C_{1-4}$alkyl substituted by chloro, bromo, phenyl or hydroxy, and
Y' is hydroxy, —NR$_{21}$R$_{22}$, C$_{5-6}$cycloalkylamino, anilino or substituted anilino having, on the phenyl ring, 1 or 2 substituents selected from halo, $C_{1-4}$alkyl, $C_{1-4}$alkoxy, hydroxy and phenoxy,
wherein each of $R_{21}$ and $R_{22}$ is independently hydrogen, $C_{1-4}$alkyl or $C_{1-4}$alkyl substituted by chloro, bromo, phenyl or hydroxy.

15. A compound according to claim 14, or an external salt thereof,
wherein
each T$_a$ is independently —NR$_2'$—Q—NR$_3'$R$_4'$,
wherein
$R_2'$ is hydrogen or methyl,
each of $R_3'$ and $R_4'$ is independently hydrogen, $C_{1-6}$alkyl, n-$C_{2-3}$hydroxyalkyl or benzyl or
$R_3'$ and $R_4'$ taken together and with the nitrogen atom to which they are joined are pyrrolidino, piperidino or morpholino, and
Q is linear or branched $C_{2-6}$alkylene.

16. A compound according to claim 14 having the formula

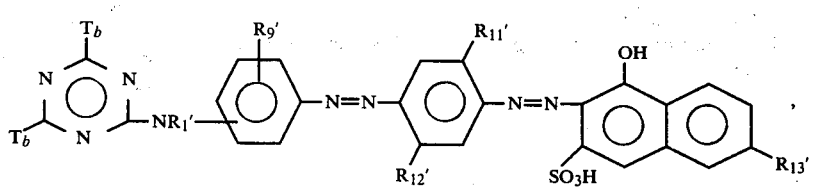

or an external salt thereof,
wherein
$R_1'$ is hydrogen or methyl,
$R_9'$ is hydrogen, chloro, methyl, methoxy, acetamido, benzamido, sulfamoyl or carbamoyl,
$R_{11}'$ is hydrogen, methyl or methoxy,
$R_{12}'$ is hydrogen, methyl or methoxy,
$R_{13}'$ is hydrogen, amino, acetamido or benzamido, and
each T$_b$ is independently —NR$_2'$—Q—NR$_3''$R$_4''$ or —NR$_2'$—Q—N$^\oplus$R$_5''$R$_6''$R$_7'$,
wherein
$R_2'$ is hydrogen or methyl, each of $R_3''$ and $R_4''$ is independently hydrogen, $C_{1-4}$alkyl or hydroxyethyl, each of $R_5''$ and $R_6''$ is independently $C_{1-4}$alkyl or hydroxyethyl or $R_3''$ and $R_4''$ or $R_5''$ and $R_6''$ taken together and with the nitrogen atom to which they are joined are piperidino or morpholino, $R_7'$ is methyl, ethyl or benzyl, and Q is linear or branched $C_{2-6}$alkylene, with the provisos that (i) each basic group is independently in free base, internal salt or acid addition salt form, (ii) the positive charge of each cationic group is independently balanced by the negative charge of the $-SO_3^\ominus$ group of the molecule or an external non-chromophoric anion, and (iii) the maximum number of basic groups in internal salt form and cationic groups the positive charge of which is balanced by the negative charge of a $-SO_3^\ominus$ group of the molecule is one.

17. A compound according to claim 16, or an external salt thereof,
wherein
each $T_b$ is independently $-NR_2'-Q-NR_3''R_4''$,
wherein
$R_2'$ is hydrogen or methyl,
each of $R_3''$ and $R_4''$ is independently hydrogen, $C_{1-4}$alkyl or hydroxyethyl or
$R_3''$ and $R_4''$ taken together and with the nitrogen atom to which they are joined are piperidino or morpholino, and
Q is linear or branched $C_{2-6}$alkylene.

18. The compound according to claim 17 having the formula

19. The compound according to claim 17 having the formula

20. A compound according to claim 17, or an external salt thereof,
wherein
$R_9'$ is hydrogen, chloro, methyl, methoxy, acetamido or benzamido,
$R_{11}'$ is hydrogen,
$R_{12}'$ is hydrogen, and
each $T_b$ is independently $-NR_2'-(CH_2)_s-NR_3''R_4''$,
wherein
$R_2'$ is hydrogen or methyl, each of $R_3''$ and $R_4''$ is independently hydrogen, $C_{1-4}$alkyl or hydroxyethyl or $R_3''$ and $R_4''$ taken together and with the nitrogen atom to which they are joined are piperidino or morpholino, and s is 2 to 6, inclusive.

21. A compound according to claim 20, or an external salt thereof,
wherein
$R_9'$ is hydrogen, and
each $T_b$ is independently $-NR_2'-(CH_2)_t-NR_3'''R_4'''$,
wherein
$R_2'$ is hydrogen or methyl,
each of $R_3'''$ and $R_4'''$ is independently methyl or ethyl, and
t is 2 or 3.

22. A compound according to claim 21, or an external salt thereof,
wherein
$R_1'$ is hydrogen, and
each $R_2'$ is hydrogen.

23. An external salt according to claim 16
wherein
$R_9'$ is hydrogen,
$R_{11}'$ is hydrogen, and
$R_{12}'$ is hydrogen, and
each $T_b$ is independently $-NR_2'-(CH_2)_t-N^\oplus(CH_3)_3$,
wherein
$R_2'$ is hydrogen or methyl, and
t is 2 or 3.

24. An external salt according to claim 23 wherein each $R_2'$ is hydrogen.

25. A compound according to claim 14 having the formula or an external salt thereof, wherein
$R_1'$ is hydrogen or methyl,
$R_9'$ is hydrogen, chloro, methyl, methoxy, acetamido, benzamido, sulfamoyl or carbamoyl,
$R_{10}'$ is hydrogen, chloro, methyl or methoxy,
$R_{11}'$ is hydrogen, methyl or methoxy,
$R_{12}'$ is hydrogen, methyl or methoxy, and
each $T_b$ is independently $-NR_2'-Q-NR_3''R_4''$ or $-NR_2'-Q-N^{\oplus}R_5''R_6''R_7'$,
wherein
$R_2'$ is hydrogen or methyl,
each of $R_3''$ and $R_4''$ is independently hydrogen, $C_{1-4}$alkyl or hydroxyethyl,
each of $R_5''$ and $R_6''$ is independently $C_{1-4}$-alkyl or hydroxyethyl or
$R_3''$ and $R_4''$ or $R_5''$ and $R_6''$ taken together and with the nitrogen atom to which they are joined are piperidino or morpholino, and
Q is linear or branched $C_{2-6}$alkylene,
with the provisos that (i) each basic group is independently in free base, internal salt or acid addition salt form, (ii) the positive charge of each cationic group is independently balanced by the negative charge of the $-SO_3^{\oplus}$ group of the molecule or an external non-chromophoric anion, and (iii) the maximum number of basic groups in internal salt form and cationic groups the positive charge of which is balanced by the negative charge of the $-SO_3^{\ominus}$ group of the molecule is one.

26. A compound according to claim 25, or an external salt thereof,
wherein each
$T_b$ is independently $-NR_2'-Q-NR_3''R_4''$,
wherein
$R_2'$ is hydrogen or methyl,
each of $R_3''$ and $R_4''$ is independently hydrogen, $C_{1-4}$alkyl or hydroxyethyl or
$R_3''$ and $R_4''$ taken together and with the nitrogen atom to which they are joined are piperidino or morpholino, and
Q is linear or branched $C_{2-6}$alkylene.

27. A compound according to claim 26, or an external salt thereof,
wherein
$R_9'$ is hydrogen, chloro, methyl, methoxy, acetamido or benzamido,
$R_{10}'$ is hydrogen,
$R_{11}'$ is hydrogen,
$R_{12}'$ is hydrogen, and
each $T_b$ is independently $-NR_2'-(CH_2)_s-NR_3''R_4''$,
wherein
$R_2'$ is hydrogen or methyl,
each of $R_3''$ and $R_4''$ is independently hydrogen, $C_{1-4}$alkyl or hydroxyethyl or
$R_3''$ and $R_4''$ taken together and with the nitrogen atom to which they are joined are piperidino or morpholino, and
s is 2 to 6, inclusive.

28. A compound according to claim 27, or an external salt thereof,
wherein each
$T_b$ is independently $-NR_2'-(CH_2)_t-NR_3'''R_4'''$,
wherein
$R_2'$ is hydrogen or methyl,
each of $R_3'''$ and $R_4'''$ is independently methyl or ethyl, and
t is 2 or 3.

29. A compound according to claim 28, or an external salt thereof,
wherein
$R_1'$ is hydrogen, and
each $R_2'$ is hydrogen.

30. The compound according to claim 29 having the formula

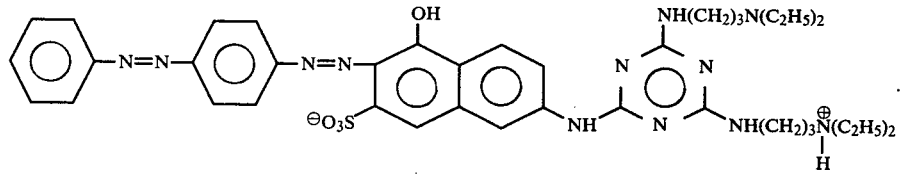

31. An external salt according to claim 25
wherein $R_9'$ is hydrogen, chloro, methyl, methoxy, acetamido or benzamido,
$R_{10}'$ is hydrogen,
$R_{11}'$ is hydrogen,
$R_{12}'$ is hydrogen, and
each $T_b$ is independently $-NR_2'-(CH_2)_t-N^{\oplus}(CH_3)_3$,
wherein
$R_2'$ is hydrogen or methyl, and
t is 2 or 3.

32. An external salt according to claim 31 wherein each $R_2'$ is hydrogen.

33. An external salt according to claim 29 having the formula

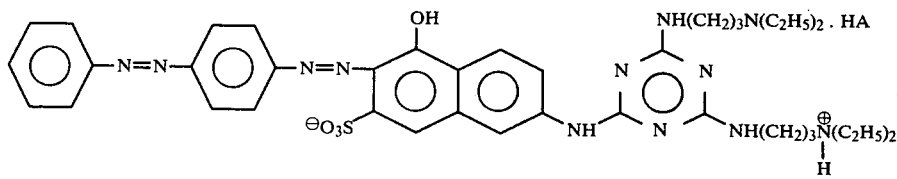

wherein HA is acetic acid, hydrochloric acid, sulfuric acid, phosphoric acid, formic acid or lactic acid.

34. The external salt according to claim 33 having the formula